United States Patent
Truong-Le

(10) Patent No.: US 8,343,518 B2
(45) Date of Patent: Jan. 1, 2013

(54) PRESERVATION OF BIOACTIVE MATERIALS BY FREEZE DRIED FOAM

(75) Inventor: Vu Truong-Le, Campbell, CA (US)

(73) Assignee: MedImmune, LLC, Gaithersburg, MD (US)

( * ) Notice: Subject to any disclaimer, the term of this patent is extended or adjusted under 35 U.S.C. 154(b) by 0 days.

(21) Appl. No.: 13/272,037

(22) Filed: Oct. 12, 2011

(65) Prior Publication Data

US 2012/0027797 A1    Feb. 2, 2012

Related U.S. Application Data

(60) Division of application No. 11/978,948, filed on Oct. 29, 2007, now Pat. No. 8,067,017, which is a continuation of application No. 11/520,503, filed on Sep. 12, 2006, now Pat. No. 7,381,425, which is a division of application No. 10/412,630, filed on Apr. 10, 2003, now Pat. No. 7,135,180.

(60) Provisional application No. 60/372,236, filed on Apr. 11, 2002.

(51) Int. Cl.
*A61K 9/12* (2006.01)
*A61K 39/285* (2006.01)

(52) U.S. Cl. ........ 424/400; 435/260; 435/246; 424/450; 424/184.1; 424/93.1; 424/93.4; 424/532

(58) Field of Classification Search ........................ None
See application file for complete search history.

(56) References Cited

U.S. PATENT DOCUMENTS

| 5,098,893 | A | 3/1992 | Franks et al. |
| 5,290,765 | A | 3/1994 | Wettlaufer et al. |
| 5,382,437 | A | 1/1995 | Ecanow |
| 5,766,520 | A | 6/1998 | Bronshtein |
| 6,267,958 | B1 | 7/2001 | Andya et al. |
| 6,306,345 | B1 | 10/2001 | Bronshtein et al. |
| 6,355,699 | B1 | 3/2002 | Vyakarnam et al. |
| 6,509,146 | B1 | 1/2003 | Bronshtein |
| 8,067,017 | B2 * | 11/2011 | Truong-Le .................... 424/400 |
| 2004/0018506 | A1 | 1/2004 | Koehler et al. |

FOREIGN PATENT DOCUMENTS

| GB | 930000 | 1/1961 |
| WO | WO 98/02240 A1 | 1/1998 |
| WO | WO 01/37804 | 5/2001 |

OTHER PUBLICATIONS

Kagumba (1977) "Lyophilisation of T1 broth culture vaccine of mycoplasma var mycoides." *Bulletin of Animal Health and Production in Africa* 25(2):116-121.

Langure et al. (1985) "Freeze-dried vaccine against rinderpest: Stability and activity study." *Comparative Immunology Microbiology and Infectious Diseases* 8(3/4): 285-296.

* cited by examiner

*Primary Examiner* — Bejamin P Blumel

(57) ABSTRACT

This invention provides methods and compositions to preserve bioactive materials in a dried foam matrix. Methods provide non-boiling foam generation and penetration of preservative agents at temperatures near the phase transition temperature of the membranes.

22 Claims, 8 Drawing Sheets

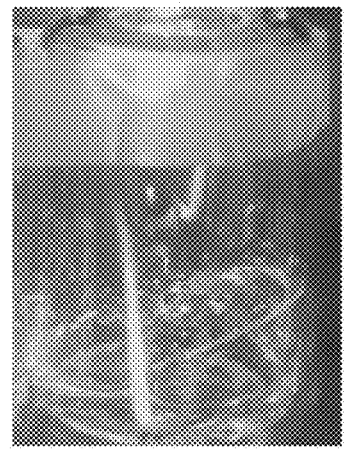
Fig. 2A
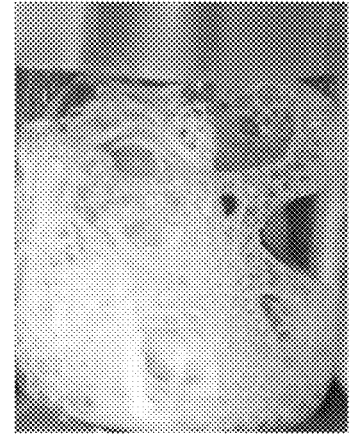
Fig. 2B
Fig. 2C
Fig. 2C
Fig. 2

PRESERVATION OF BIOACTIVE MATERIALS BY FREEZE DRIED FOAM

CROSS-REFERENCE TO RELATED APPLICATIONS

This application is a Divisional application claiming benefit of and priority of a prior parent utility application Ser. No. 11/978,948, "Dried Foam Preservation of Bioactive Materials", filed Oct. 29, 2007, which is a Continuation application claiming priority to and benefit of a prior to parent Utility application Ser. No. 11/520,503 "Dried Foam Preservation of Bioactive Materials a Divisional Application" by Vu Truong-Le, filed Sep. 12, 2006 (now U.S. Pat. No. 7,381,425); which is a Divisional application from U.S. Utility application Ser. No. 10/412,630, "Dried Foam Preservation of Bioactive Materials" by Vu Truong-Le, filed Apr. 10, 2003 (now U.S. Pat. No. 7,135,180), which claims priority to and benefit of prior U.S. Provisional Application No. 60/372,236, "Formulations and Methods for Preparation" by Vu Truong-Le, filed Apr. 11, 2002. The full disclosure of the prior application is incorporated herein by reference.

FIELD OF THE INVENTION

The present invention is in the field of preservation of biologic materials in storage. In particular, the invention relates to, e.g., preservation of bioactive molecules and viable membranous biologics by glassification in a protective dry foam matrix.

BACKGROUND OF THE INVENTION

Biological materials, such as proteins, eukaryotic cells, bacteria and viruses, are generally unstable when stored in media or other liquid solutions. For example, enveloped viruses such as live influenza virus manufactured from egg allantoid fluid loose one log of potency, defined as Tissue Culture Infectious Dose (TCID50), in less than two to three weeks when stored under refrigerated temperature, i.e. approximately 4° C. At room temperature conditions (approximately 25° C.) and at warmer temperatures such as 37° C., the virus looses the such potency in a matter of days to hours, respectively. Lyophilization processes, where aqueous formulas are frozen and then dried by sublimation, are commonly used to stabilize these biological materials. Removal of water and substitution of protectant molecules, such as carbohydrates, can increase stability by preventing chemical degradation, denaturation, and growth of microbial contaminants.

In lyophilization (freeze-drying), the biological material is commonly mixed as a solution or suspension with protective agents, frozen, and then dehydrated by sublimation and secondary drying. The low temperatures of freezing and drying by sublimation can slow the kinetics of degradation reactions. However, the low temperatures and low surface to volume ratios involved can require long drying time periods. Often significant structural damage results in conventional freeze drying processes due to the slow freezing rate and the length of time bioactive material is kept in a frozen state. This damage can involve denaturation, aggregation, and other untoward physical stresses stemming from the ice crystal structures that are formed during the ice nucleation and propagation steps. For this reason, biomaterials that possess a cell wall or lipid membrane pose a significant challenge to preserving the bioactivity of larger and more complex entities such as viruses, bacteria, and cells.

Additionally, even under optimal freeze drying conditions, damage can occur during the secondary drying step. A recent study has suggested freeze drying induced damage occurs primarily during the secondary dehydration step when the last remaining amount of water is removed (Webb, S. D. Effects of annealing lyophilized and spray-lyophilized formulations of recombinant human interferon-gamma. J Pharm Sci 2003 April; 92(4):715-29). Therefore, there is sufficient evidence to show that lyophilization and secondary drying processes can force a protein or cell, for example, to undergo significant chemical and physical changes. Such changes can result in loss of activity of the protein due to concentration of salts, precipitation/crystallization, shear stress, pH extremes, and residual moisture remaining through the freeze-drying.

Protective agents are chemicals that are added to a formulation to protect cells and molecules during freezing and to enhance stability during storage. For example, stabilizers for live virus vaccines generally include high concentrations of sugars such as sucrose, mannitol, or sorbitol to improve virus stability during lyophilization and storage. However, with membrane viruses, and other membranous biologicals, the protective agents may not penetrate adequately to protect active molecules within the membrane volume. Therefore a significant challenge remains to develop an optimal drying process and formulation to achieve adequate stability for thermally labile biologics.

Some of the problems with lyophilization are overcome by certain dry foam preservation processes. In U.S. Pat. No. 5,766,520, Preservation by Foam Formation, to Bronshtein, for example, biological solutions or suspensions in a solvent are thickened by first drying under a moderate vacuum before application of a strong vacuum to cause frothy boiling of the remaining solvent to form a dry stable foam. Normally, such boiling is avoided in processing of biological materials due to the oxidation and denaturation that can occur on bubble surfaces. In addition, boiling, even under vacuum, requires input of heat, which can endanger the stability of the bioactive material. These problems are reduced in Bronshtein by including protective agents, such as carbohydrates and surfactants, in the solution or suspension. Dry foam preservation processes of this type have the advantage of faster drying due to convection of the liquid during boiling and the large surface area presented by the foam. Reconstitution of such a dry foam can be rapid due to the presence of the hydrophilic protective agents and the large foam surface area. The dry foam can be milled to a fine powder to further improve reconstitution times or for administration of the biological material by inhalation.

The dry foam preservation processes described above is limited in its flexibility to protect a variety of biological materials. For example, the process rules out a freezing step and subsequent sublimation of the ice as a means to remove water from the foam. In the case of highly thermolabile materials, a freezing step can provide stability over the course of dehydration. Because freezing is avoided in Bronshtein, the formulation must be thickened before foaming and drying so that large amounts of water are not lost, along with latent heat, to freeze the foam. The avoidance of freezing requires the process to be conducted at lower vacuum level (7-24 Torr) than in conventional freeze drying or spray freeze drying process cycles. Boiling in Bronshtein, requires input of significant, and possibly destabilizing, amounts of heat to provide the necessary eruption of foam.

The Bronshtein dry foam process is not particularly well adapted to preservation of biological materials having lipid membranes. For example, the process is not well adapted to preservation of membranous biologicals, such as liposomes, viruses or viable cells. Lipid membranes often prevent penetration of the protective agents into enclosed volumes or prevent adequate removal of water from the enclosed volume. Without adequate penetration of protective agents, enzymatic processes, such as proteolysis, and chemical processes, such as oxidation and free radical attacks, can destroy the activity or viability of the membranous biological material. Hypoosmotic fluids remaining within membrane enclosed volumes can promote instability of the biological material.

A need remains for methods to preserve biological materials, such as proteins and membranous materials in storage, particularly at temperatures above freezing. Methods to prepare dry foam preservation matrices through processes with optional freezing and optional boiling steps, are desirable to suit the sensitivities of particular biologic materials. Compositions that can protect such biologicals in storage would provide benefits in medicine and scientific research. The present invention provides these and other features that will become apparent upon review of the following.

SUMMARY OF THE INVENTION

The present invention includes methods and compositions for preserving bioactive materials in storage. The methods generally provide, e.g., processes of expanding a formulation of the bioactive material and a polyol into a foam followed by drying the foam into a stable dry foam composition. The methods can variously include, e.g., freezing of the foam before drying, inclusion of foaming agents in the formulation, holding the formulation at the phase transition temperature of a lipid membrane to enhance penetration of protective agents, and/or expansion of the formulation at pressures between about 200 Torr and 25 mTorr.

A stable dry foam composition to preserve bioactive materials having lipid membranes can be prepared using the methods of the invention. The methods generally include, e.g., preparing a formulation of a polyol or polymer in a solvent (such as water or an alcohol) with the bioactive material, cooling the formulation to a temperature of about the phase transition temperature of the lipid membrane, expanding the formulation into a foam, and drying the foam by evaporation or sublimation to prepare a stable dry foam composition of the lipid membrane containing bioactive material. For example, a formulation of a live attenuated influenza virus with about 40% sucrose, 5% gelatin, 0.02% block copolymers of polyethylene and polypropylene glycol, and 25 mM 7.2 pH $KPO_4$ buffer can be aliquoted into glass lyophilization vials, cooled at a phase transition temperature of about 15° C. for about 30 minutes, expanded in a vacuum of about 50 mTorr for about one hour, and exposed to a drying temperature of about 33° C. for about 48 hours before sealing the vials. The dry foam composition prepared by such a process can remain stable for at least about 2 years in storage at about 25° C.

Another method of the invention calls for expanding the formulation into a foam at vacuum pressures higher than those described in the prior art. For example, a formulation of a bioactive material (including membranes or not) in a solvent with a polyol or polymer, can be expanded into a foam (without requiring foaming agents) by exposure to a pressure less than 25 Torr, less than 8 Torr, less than 400 mTorr, or between about 200 mTorr and 25 mTorr, and the foam physically stabilized and dried by evaporation or sublimation of the solvent from the foam to prepare a dry foam composition.

Foaming agents can be provided in methods and formulations of the invention to provide adequate foaming under conditions not described in the prior art. In the prior art, foaming action can be rapid, violent, and difficult to control. Furthermore, the foams described elsewhere are almost exclusively closed cell, i.e. the roof of the foam structure is a continuous layer with no openings to provide for transfer of heat and moisture. This can result in foams lacking uniformity in moisture content and glass transition properties. In the present invention, a formulation (suspension or solution) of a bioactive material, a foaming agent, and a polyol or polymer in a solvent can be prepared, the formulation expanded into a foam with the bubbles generated by boiling or provided by the action of a foaming agent, and the foam can be stabilized and dried by evaporating or sublimating the solvent from the foam. Foaming agents can provide bubbles for expansion of formulations, e.g., generating gas bubbles in situ and/or by providing a suspension of small bubbles for expansion under a vacuum. For example, bubbles can be generated by boiling the agent, degassing the formulation, acidifying a carbonate, hydrating an active metal, electrolysis of water, and/or the like. Bubbles can be suspended in the formulation before expansion by, e.g., boiling, degassing, chemical generation of gasses, mechanical whipping of the formulation, injection of bubbles into the formulation, and/or the like. For example, a formulation of a bioactive material (including membranes or not) in a solvent with a polyol or polymer, can be expanded into a foam (by the action of the foaming agents) by exposure to a pressure less than 400 Torr, or between about 200 Torr and 25 Torr, or between 25 Torr and 7.7 Torr, and the foam physically stabilized and dried by evaporation or sublimation of the solvent from the foam to prepare a dry foam composition.

Methods of the invention can provide a lyophilized dry foam composition by freeze drying expanded foams. A formulation of bioactive material, a polyol or a polymer can be prepared, the pressure reduced on the formulation to expand a foam, the foam frozen, and the frozen foam dried by sublimation to provide a lyophilized dry foam composition. In methods where formulations are frozen, the freezing can be, e.g., by loss of latent heat, and/or conduction to a cold solid or fluid environment.

Compositions of the invention can be prepared, e.g., according to the methods of the invention above. Formulations for preparation of the compositions can include, e.g., a solvent, a bioactive material, a polyol, a polymer, a foaming agent, a surfactant and/or a buffer. Total solids (e.g., formulation constituents other than solvents) in the formulations can range, e.g., from less than about 30 weight percent to about 70 weight percent.

Bioactive materials preserved by the methods of the invention can include, e.g., peptides, proteins, nucleic acids, antibodies, vaccines, bacteria, viruses, liposomes, platelets, cell suspensions and/or the like. The viruses can be, e.g., live viruses, attenuated viruses, and/or non-viable viruses, such as influenza virus, parainfluenza virus, AAV, adenovirus, respiratory syncytial virus, SARS (severe acute respiratory syndrome) virus, herpes simplex virus, cytomegalovirus, corona virus family members, human metapneumovirus, Epstein-Barr virus, and/or the like. Viruses in formulations of the methods can be present, e.g., in an amount ranging about $10^3$ $TCID_{50}/mL$ to about $10^{12}$ $TCID_{50}/mL$, or from about $10^6$ $TCID_{50}/mL$ to about $10^9$ $TCID_{50}/mL$. Dried foam compositions of the invention can provide virus present in an amount, e.g., from about $10^1$ $TCID_{50}/g$ to not more than $10^{12}$ $TCID_{50}/g$. Dried foam compositions can provide virus present in an amount, e.g., of about $10^2$ $TCID_{50}/g$, about $10^2$ $TCID_{50}/g$, about $10^3$ $TCID_{50}/g$, about $10^4$ $TCID_{50}/g$, about $10^5$ $TCID_{50}/g$, about $10^6$ $TCID_{50}/g$, about $10^7$ $TCID_{50}/g$, about $10^8$ $TCID_{50}/g$, about $10^9$ $TCID_{50}/g$, about $10^{10}$ $TCID_{50}/g$, or about $10^{11}$ $TCID_{50}/g$.

The polyols of the invention can include, e.g., non-reducing sugars, reducing sugars, sugar alcohols and sugar acids. Polyols can act as, e.g., protective agents and structural constituents of stabilized foam in the invention. Polyols can include, e.g., sucrose, trehalose, sorbose, melezitose, sorbitol, stachyose, raffinose, fructose, mannose, maltose, lactose, arabinose, xylose, ribose, rhamnose, galactose and glucose, mannitol, xylitol, erythritol, threitol, sorbitol, glycerol, L-gluconate, and/or the like. The polyol can be present in the formulation in an amount ranging from about 1 weight percent to about 45 weight percent, about 5 weight percent to about 40 weight percent, or at about 20 weight percent.

Polymers can be present in the formulations and compositions of the invention to provide, e.g., stability to bioactive materials and to act as structural constituents in the dried foam compositions. Polymers of the methods and compositions can include, e.g., hydrolyzed gelatin, unhydrolyzed gelatin, collagen, chondroitin sulfate, a sialated polysaccharide, actin, myosin, water soluble polymers such as polyvinyl pyrrolidone, microtubules, dynein, kinetin, human serum albumin, and/or the like. The polymers can be present, e.g., in the formulations of the methods in an amount ranging from about 1 weight percent to about 10 weight percent. In one embodiment the polymer is human serum albumin present in the formulation at about 5 weight percent.

Surfactants can be present in the formulations and compositions of the invention, e.g., to stabilize and enhance the solubility of other constituents. Surfactants of the formulations and compositions can include, e.g., polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde, or condensates of sulfonated naphthalenes with formaldehyde and phenol, lignin-sulfite waste liquor, alkyl phosphates, quaternary ammonium compounds, amine oxides, betaines, and/or the like. Tween® and Pleuronic® surfactants, such as, e.g., polyethylene glycol sorbitan monolaurate, polyoxyethylenesorbitan monooleate, or block copolymers of polyethylene and polypropylene glycol, are particularly preferred surfactants of the invention. Surfactants can be present in formulations of the invention in amounts of about 0.01 weight percent to about 1 weight percent.

Buffers can be included in formulations and compositions of the invention, e.g., to stabilize other constituents, control pH, and/or to participate in foaming processes. Typical buffers of the invention are, e.g., potassium phosphate, sodium phosphate, sodium acetate, sodium citrate, sodium succinate, histidine, imidazole, ammonium bicarbonate, or a carbonate. pH levels can be adjusted in the formulations, compositions, and reconstituted products of the invention, e.g., to a pH ranging from about pH 4 to about pH 10, from about pH 6 to about pH 8, and, more typically, near neutral or about pH 7.2.

In methods of the invention, formulations can be cooled, e.g., before expansion, to thicken the formulation, to effect freezing during preliminary drying, to enhance penetration of protective agents through lipid membranes at phase transition temperatures, and/or the like. Cooling to the phase transition temperature of lipid membranes can involve, e.g., adjusting the formulation to a temperature ranging from about 2° C. to about 70° C., 10° C. to 45° C., or about 12° C. to about 16° C. To obtain adequate penetration of protective agents, such as polyols and/or polymers, the formulation can be held at the phase transition temperature for about 10 minutes to about 60 minutes, or for about 30 minutes.

In methods of the invention, formulations can be held, e.g., in temperature controlled and/or pressure controlled chambers. During expansion, foam stabilization, primary drying, and/or secondary drying stages, the pressure of gasses in the environment of the formulations can be reduced to less than about 400 Torr, about 200 Torr or less, between about 100 Torr and about 25 Torr or less, between 25 Torr and 7.7 Torr or less, between 2500 mTorr and about 50 mTorr, or about 25 mTorr or less. The vacuum can be maintained, e.g., for expansion, foam stabilization, or primary drying for a time ranging from about one hour to about two hours.

Secondary drying of the dry foam can proceed, e.g., to further reduce residual moisture in the stabilized foam and/or dry foam of the methods and compositions of the invention. For example, secondary drying can be initiated by increasing the temperature of the formulation to a drying temperature that is less than or about the glass transition temperature of the dry foam. Drying temperatures can range, e.g., from about 10° C. to about 70° C., or from about 30° C. to about 35° C. Moisture can be removed from the gaseous environment around the foam, e.g., by desiccation and/or condensation, to help drive the drying process to a desired end point. In secondary drying, the dried foam can be held, e.g., at reduced pressure and at the drying temperature for a time ranging from about 6 hours to about 5 days, or about 48 hours. Secondary drying can continue, e.g., until the residual moisture content of the stable composition ranges from about 0.1% to about 5%.

To provide convenient and stable dosage forms, formulations can be filled into suitable containers. Containers can be provided with etched bottoms, e.g., promote bubble formation at the bottom of the container and/or to generate an open cell foam during foam expansion process steps. The container can be aseptically sealed, e.g., with a stopper to retain a vacuum and/or inert gas environment over the stable compositions of the invention.

In one embodiment, the composition of the invention can be a dry foam composition of a bioactive material comprising a lipid membrane enclosed compartment and a polyol or polymer that has penetrated the lipid membrane into the enclosed compartment. In this embodiment, the polyol and/or polymer protective agents penetrated the lipid membrane while at about the phase transition temperature of the membrane.

The compositions of the invention can be prepared, e.g., by the methods of the invention. For example, a dry foam composition with improved stability and shelf-life can be prepared by: preparing a formulation of a bioactive material (with or without lipid membranes) a polyol or a polymer, with or without a foaming agent; optionally, cooling the formulation to a temperature of about a phase transition temperature of any relevant lipid membranes; reducing pressure (optionally, from about 200 Torr to about 25 Torr, 7.7 Torr, 2.5 Torr, 50 mTorr, or less) on the formulation to form a foam, which is optionally frozen and the ice sublimated; drying the foam to stabilize the physical structure and/or to provide a dry foam composition.

Compositions of the invention can be administered to mammals, such as humans, as vaccines, therapeutics, pharmaceuticals, and/or the like. The compositions can be administered, e.g., as ground powders by inhalation or as reconstituted liquids by injection. The dry foam compositions of the invention can be ground, e.g., to a stable powder compositions with any desired size range, for example, an average particle size from about 0.1 um to about 150 um, or about 10 um to about 100 um, for quick reconstitution or delivery by inhalation. Reconstituted liquid can be administered by, e.g., delivering the composition to the mammal by intravenous, intramuscular, intraperitoneal, intracerebrospinal, subcutaneous, intra-articular, intrasynovial, intrathecal, oral, topical, intranasal, and/or pulmonary routes. Administering bioactive material in methods and compositions of the invention typically involves, e.g., delivery of a dose ranging from about 0.01 ng/kg to about 15 mg/kg.

Definitions

It is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a surface" includes a combination of two or more surfaces; reference to "bacteria" includes mixtures of bacteria, and the like.

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used in accordance with the definitions set out below.

"Ambient" temperatures or conditions are those at any given time in a given environment. Typically, ambient room temperature is 22° C., ambient atmospheric pressure, and ambient humidity are readily measured and will vary depending on the time of year, weather conditions, altitude, etc.

"Boiling" refers, e.g., to the rapid phase transition from liquid to gas that takes place when the temperature of a liquid is above its boiling temperature. The boiling temperature, as is well known to those skilled in the art, is the temperature at which the vapor pressure of a liquid is equal to the applied pressure.

"Buffer" refers to a buffered solution that resists changes in pH by the action of its acid-base conjugate components. The pH of the buffer will generally be chosen to stabilize the active material of choice, and will be ascertainable by those in the art. Generally, this will be in the range of physiological pH, although some proteins, can be stable at a wider range of pHs, for example acidic pH. Thus, preferred pH ranges are from about 1 to about 10, with from about 3 to about 8 being particularly preferred; more preferably, from about 6.0 to about 8.0; yet more preferably, from about 7.0 to about 7.4; and most preferably, at about 7.0 to about 7.2. Suitable buffers include a pH 7.2 phosphate buffer and a pH 7.0 citrate buffer. As will be appreciated by those in the art, there are a large number of suitable buffers that may be used. Suitable buffers include, but are not limited to, potassium phosphate, sodium phosphate, sodium acetate, histidine, imidazole, sodium citrate, sodium succinate, ammonium bicarbonate and carbonate. Generally, buffers are used at molarities from about 1 mM to about 2 M, with from about 2 mM to about 1 M being preferred, and from about 10 mM to about 0.5 M being especially preferred, and 25 to 50 mM being particularly preferred.

"Degassing" refers to the release of a gas from solution in a liquid when the partial pressure of the gas is greater than the applied pressure. If water is exposed to nitrogen gas at one atmosphere (about 760 Torr), and the partial pressure of nitrogen in the water equilibrates to the gas phase pressure, nitrogen can bubble from the water if the gas pressure is reduced. This is not boiling, and can often occur at pressures above a pressure that would boil a solvent. For example, bottled carbonated soft drinks, with a high partial pressure of $CO_2$ gas, bubble rapidly (but do not boil) when pressure is reduced by removing the bottle cap.

"Dispersibility" means the degree to which a powder composition can be dispersed (i.e. suspended) in a current of air so that the dispersed particles can be respired or inhaled into the lungs of a subject. Thus, a powder that is only 20% dispersible means that only 20% of the mass of particles can be suspended for inhalation into the lungs.

"Dry" in the context of dried foam compositions refers to residual moisture content less than about 10%. Dried foam compositions are commonly dried to residual moistures of 5% or less, or between about 3% and 0.1%. A "dry foam" can be a stabilized foam with less than 10% residual moisture content, a foam after primary drying, and/or a foam after secondary drying. “Dry” in the context of particles for inhalation means that the composition has a moisture content such that the particles are readily dispersible in an inhalation device to form an aerosol.

“Excipients” or “protectants” (including cryoprotectants and lyoprotectants) generally refer to compounds or materials that are added to ensure or increase the stability of the therapeutic agent during the spray freeze dry process and afterwards, for long term stability and flowability of the powder product. Suitable excipients are generally relatively free flowing particulate solids, do not thicken or polymerize upon contact with water, are basically innocuous when inhaled by a patient and do not significantly interact with the therapeutic agent in a manner that alters its biological activity. Suitable excipients are described below and include, but are not limited to, proteins such as human and bovine serum albumin, gelatin, immunoglobulins, carbohydrates including monosaccharides (galactose, D-mannose, sorbose, etc.), disaccharides (lactose, trehalose, sucrose, etc.), cyclodextrins, and polysaccharides (raffinose, maltodextrins, dextrans, etc.); an amino acid such as monosodium glutamate, glycine, alanine, arginine or histidine, as well as hydrophobic amino acids (tryptophan, tyrosine, leucine, phenylalanine, etc.); a methylamine such as betaine; an excipient salt such as magnesium sulfate; a polyol such as trihydric or higher sugar alcohols, e.g. glycerin, erythritol, glycerol, arabitol, xylitol, sorbitol, and mannitol; propylene glycol; polyethylene glycol; Pluronics; surfactants; and combinations thereof.

“Glass” or “glassy state” or “glassy matrix,” refers to a liquid that has lost its ability to flow, i.e. it is a liquid with a very high viscosity, wherein the viscosity ranges from $10^{10}$ to $10^{14}$ pascal-seconds. It can be viewed as a metastable amorphous system in which the molecules have vibrational motion but have very slow (almost immeasurable) rotational and translational components. As a metastable system, it is stable for long periods of time when stored well below the glass transition temperature. Because glasses are not in a state of thermodynamic equilibrium, glasses stored at temperatures at or near the glass transition temperature relax to equilibrium and lose their high viscosity. The resultant rubbery or syrupy, flowing liquid is often chemically and structurally destabilized. While a glass can be obtained by many different routes, it appears to be physically and structurally the same material by whatever route it was taken. The process used to obtain a glassy matrix for the purposes of this invention is generally a solvent sublimation and/or evaporation technique.

The "glass transition temperature" is represented by the symbol $T_g$ and is the temperature at which a composition changes from a glassy or vitreous state to a syrup or rubbery state. Generally $T_g$ is determined using differential scanning calorimetry (DSC) and is standardly taken as the temperature at which onset of the change of heat capacity (Cp) of the composition occurs upon scanning through the transition. The definition of $T_g$ is always arbitrary and there is no present international convention. The $T_g$ can be defined as the onset, midpoint or endpoint of the transition; for purposes of this invention we will use the onset of the changes in Cp when using DSC and DER. See the article entitled "Formation of Glasses from Liquids and Biopolymers" by C. A. Angell: Science, 267, 1924-1935 (Mar. 31, 1995) and the article entitled "Differential Scanning calorimetry Analysis of Glass Transitions" by Jan P. Wolanczyk: Cryo-Letters, 10, 73-76 (1989). For detailed mathematical treatment see "Nature of the Glass Transition and the Glassy State" by Gibbs and DiMarzio: Journal of Chemical Physics, 28, NO. 3, 373-383 (March, 1958). These articles are incorporated herein by reference.

"Penetration enhancers" are surface active compounds that promote penetration of a drug through a mucosal membrane or lining and can be generally used where this feature is desirable, e.g., intranasally, intrarectally, and intravaginally.

"Pharmaceutically acceptable" excipients (vehicles, additives) are those which can reasonably be administered to a subject mammal to provide an effective dose of the active ingredient employed. Preferably, these are excipients which the Federal Drug Administration (FDA) have to date designated as 'Generally Regarded as Safe' (GRAS).

"Pharmaceutical composition" refers to preparations which are in such a form as to permit the biological activity of the active ingredients to be unequivocally effective, and which contain no additional components which are toxic to the subjects to which the composition would be administered.

A "polyol" is a substance with multiple hydroxyl groups, and includes, e.g., sugars (reducing and nonreducing sugars), sugar alcohols and sugar acids. Preferred polyols herein have a molecular weight which is less than about 600 kDa (e.g. in the range from about 120 to about 400 kDa). A "reducing sugar" is a polyol which contains a hemiacetal group that can reduce metal ions or react covalently with lysine and other amino groups in proteins. A "nonreducing sugar" is a sugar which does not have these properties of a reducing sugar. Examples of reducing sugars are fructose, mannose, maltose, lactose, arabinose, xylose, ribose, rhamnose, galactose and glucose. Nonreducing sugars include sucrose, trehalose, sorbose, melezitose and raffinose. Mannitol, xylitol, erythritol, threitol, sorbitol and glycerol are examples of sugar alcohols. As to sugar acids, these include L-gluconate and metallic salts thereof.

A "Powder" is a composition that consists of finely dispersed solid particles that are relatively free flowing and capable of being readily dispersed in an inhalation device and subsequently inhaled by a patient so that the particles are suitable for intranasal or pulmonary administration via the upper respiratory tract including the nasal mucosa.

"Recommended storage temperature" for a composition is the temperature ($T_b$) at which powdered drug composition can be stored to maintain the stability of the drug product over the shelf life of the composition in order to ensure a consistently delivered dose. This temperature is initially determined by the manufacturer of the composition and approved by the governmental agency responsible for approval the composition for marketing (e.g., the Food and Drug Administration in the U.S.). This temperature will vary for each approved drug product depending on the temperature sensitivity of the active drug and other materials in the product. The recommended storage temperature will vary from about 0° to about 40° C., but generally will be ambient temperature, i.e. about 25° C. Usually a drug product will be kept at a temperature that is at or below the recommended storage temperature.

A biologically active material "retains its biological activity" in a pharmaceutical composition, if the biological activity of the biologically active material, such as an enzyme, at a given time is within about 10% (within the errors of the assay) of the biological activity exhibited at the time the pharmaceutical composition was prepared as determined in a binding assay, for example. In the case of living viruses or bacteria, biological activity can be considered retained when the viral titer or colony count of the composition is within one log of the initial titer or count. For live cells, the biological activity is considered retained when the live cell count of the composition is within 50% of the initial count. The assay that is used to determine live influenza virus titer is the Fluorescent Focus Assay (FFA assay). The titer from this assay is reported as log Fluorescent Focus Unit per milliliter (log FFU/ml). One log FFU/ml is approximately equal to one log Tissue Culture Infectious Dose per ml (log TCID50/ml). Other "biological activity" assays are elaborated below.

A biologically active material "retains its chemical stability" in a pharmaceutical composition, if the chemical stability at a given time is such that the biologically active material is considered to retain its biological activity as defined herein. Chemical stability can be assessed by detecting and quantifying chemically altered forms of the biologically active material. Chemical alteration may involve size modification (e.g. clipping of proteins) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g. occurring as a result of deamidation) which can be evaluated by ion-exchange chromatography, for example.

A biologically active material "retains its physical stability" in a pharmaceutical composition if it shows no significant increases in aggregation, precipitation and/or denaturation upon visual examination of color and/or clarity, or as measured by UV light scattering or by size exclusion chromatography.

A "stable" formulation or composition is one in which the biologically active material therein essentially retains its physical stability and/or chemical stability and/or biological activity upon storage. Various analytical techniques for measuring stability are available in the art and are reviewed, e.g., in Peptide and Protein Drug Delivery, 247-301, Vincent Lee Ed., Marcel Dekker, Inc., New York, N.Y., Pubs. (1991) and Jones, A. Adv. Drug Delivery Rev. 10: 29-90 (1993). Stability can be measured at a selected temperature for a selected time period. Trend analysis can be used to estimate an expected shelf life before a material has actually been in storage for that time period. For live influenza viruses, stability is defined as the time it takes to loose 1 log of FFU/ml or 1 log of TCID50/ml. Preferably, the composition is stable at room temperature (~25° C.) for at least three months, or at 40° C. for at least 1 month, and/or stable at about 2-8° C. for at least 1 year. Furthermore, the composition is preferably stable following freezing (to, e.g., −70° C.) and thawing of the composition.

In a pharmacological sense, a "therapeutically effective amount" of a biologically active material refers to an amount effective in the prevention or treatment of a disorder wherein a "disorder" is any condition that would benefit from treatment with the biologically active material. This includes chronic and acute disorders or diseases including those pathological conditions which predispose the mammal to the disorder in question.

"Treatment" refers to both therapeutic treatment and prophylactic or preventative measures. Those in need of treatment include those already with the disorder as well as those in which the disorder is to be prevented.

"Unit dosage" refers to a receptacle containing a therapeutically effective amount of a composition of the invention.

BRIEF DESCRIPTION OF THE DRAWINGS

FIGS. 2A to 2D are photographic images of a formulation foam drying in glass vials.

DETAILED DESCRIPTION

Figure 1:
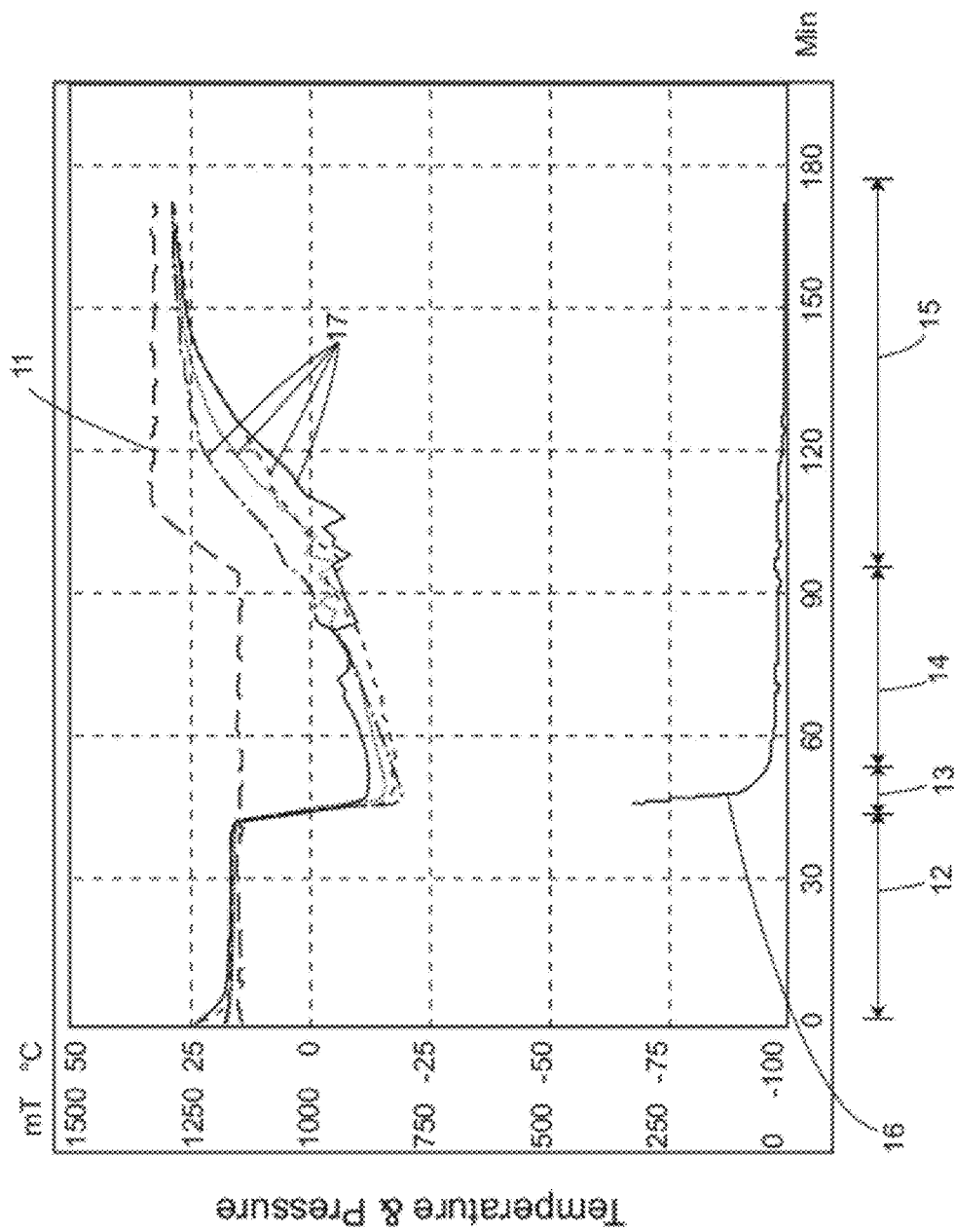
FIG. 1 is a chart of temperature and pressure versus time during an exemplary foam drying process.

The methods and compositions of the present invention can provide extended storage of bioactive materials, such as, e.g., peptides, proteins, nucleic acids, antibodies, vaccines, bacteria, viruses, liposomes, platelets, and/or cell suspensions, in a glassy matrix of a dry foam. Methods of the invention provide a dry foam preservative composition by, e.g., preparing a formulation comprising a bioactive material with a polyol or polymer in a solvent (with or without a foaming agent), reducing pressure to expand the formulation into a foam (by degassing, boiling, and/or expansion of introduced bubbles), and stabilizing the foam by evaporating or sublimating the solvent from the foam (with or without freezing the foam). In methods, e.g., particularly well suited to preservation of bioactive materials comprising lipid membranes, the bioactive material can be formulated into a suspension with protective agents, precooled, and held at a temperature near the phase transition temperature of the membrane to allow the protective agents to penetrate the membrane before expanding the formulation into a foam.

Methods of Preparing Stable Dry Foams

Methods for preparing stable dry foams for preservation of bioactive materials includes, in general, e.g., preparation of a formulation combining the bioactive material with a polyol and/or polymer in a solution or suspension, reducing the pressure applied to the formulation to initiate foaming, stabilizing the foam by removal of a solvent, and drying the foam.

In one embodiment, for example, a formulation of bioactive material, polyol and/or polymer, in a solvent, is expanded to a foam under a pressure of between about 200 Ton and about 25 Torr before stabilizing and drying the foam. This embodiment is distinguished from prior art discussed above, e.g., in not requiring a strong vacuum (pressure 24 Torr or less) in order to obtain adequate foam expansion. In this embodiment, adequate foaming can be obtained at higher pressures because the methods of the invention provide foam expansion, e.g., from degassing of saturated gasses from the formulation, boiling of high vapor pressure solvents from the formulation, gas forming chemistries, and/or enlargement of bubbles injected or trapped in the formulation. Formulations of this embodiment can be, e.g., precooled and/or lose substantial latent heat during expansion of foam or drying to, e.g., optionally result in freezing and/or lyophilization of the foam. After the primary drying stage is complete, the stabilized dry foam can be held, e.g., at secondary drying temperatures at pressures below 50 mTorr, to complete drying of the formulation.

In another embodiment, a foaming agent is present in the formulation, e.g., to provide foam expansion and/or control with or without boiling. For example, a formulation containing a foaming agent, a bioactive material, and a polyol and/or polymer, can be subjected to a reduced pressure in which the formulation is expanded into a foam (by action of the foaming agent), stabilized and dried. The foaming agent can be, e.g., gas in solution in the formulation, a high vapor pressure (volatile) solvent, a carbonate, an active metal, a direct electric current, a suspension of fine gas bubbles, and/or the like, as described below in the Foaming the Formulation section.

Another embodiment of the invention provides, e.g., methods to prepare lyophilized foam compositions for preservation of bioactive materials. For example, a formulation containing a bioactive material, and a polyol and/or polymer, can be expanded into a foam under reduced pressure, frozen and sublimated to provide a lyophilized dry foam composition. Freezing, in this embodiment, can be, e.g., by conduction of heat away from the formulation, and/or by loss of latent heat due to solvent evaporation or sublimation.

The present invention includes, e.g., methods for preservation of biological materials having a lipid membrane component. Methods for preserving bioactive materials comprising lipid membranes can include, e.g., cooling a membranous biologic material formulation to a membrane phase transition temperature of about 45° C. to 0° C. for about 30 minutes in a solution containing about 2% to 40% of a polyol protective agent. (The protective agents can, e.g., penetrate the membranes in phase transition to stabilize biological molecules within enclosed volumes. A membrane phase transition temperature is the temperature at which the lipid membrane transitions between a fluid (high mobility) phase to a more rigid gel-crystalline phase. It is postulated that because lipid membranes tend to be pervious to passive diffusion of external milieu at lipid bilayer's characteristic phase transition temperature, one way to load stabilizers/protective agents to the cells, bacteria, or viruses is by preincubating at such phase transition.) Pressure can then be reduced, e.g., to boil the formulation and produce a foam. Water can be rapidly lost from the formulation, along with latent heat, resulting, e.g., in freezing of the foam. Water continues to be lost, e.g., by sublimation over the course of several minutes to provide a substantially dry foam composition. The temperature can be warmed, e.g., to drive off additional residual moisture and water of hydration to enhance the physical and/or chemical stability of the dry foam.

FIG. 1 shows an exemplary freeze foam drying process of the invention. Superimposed on a chart of vacuum chamber temperatures and pressures versus time are photographic images of formulations containing a membrane virus at various stages of drying. Chamber temperature line 11 indicates the temperature of the vacuum chamber during the freeze foaming process. The chamber temperature is held at about the phase transition temperature of the virus, or about 15° C., through penetration stage 12, foaming stage 13, and initial drying stage 14. The chamber temperature is ramped up to drying temperatures of about 33° C. during secondary drying phase 15. Chamber pressure line 16 remains at or above atmospheric pressure during the penetration stage, drops to about 2500 mTorr during the foaming stage, about 250 mTorr during the initial drying stage, and about 50 mTorr during the secondary drying stage. Vial temperature lines 17 represent temperatures measured from thermocouples placed into formulations in representative vials during the process. The vials hold the membrane phase transition temperature during the penetration stage but chill suddenly as the pressure drops during the foaming stage due to loss of latent heat from evaporation and sublimation of water from the formulation. Vial temperatures gradually rise to near chamber drying temperatures as the rate of residual moisture loss tapers off in the secondary drying stage.

FIGS. 2A to 2D show photographic images of representative vials of formulation during stages of freeze foam drying. In FIG. 2A, liquid formulation at the bottom of the vial is beginning to boil as pressure in the chamber begins to drop. In FIG. 2B, a foamy matrix has begun to stabilize as it thickens with loss of water and lower temperatures. In FIG. 2C, the foam is frozen and has lost most of the initial drying stage water. FIG. 2D shows the dried foam glassy matrix well into the secondary drying stage.

Figure 3:
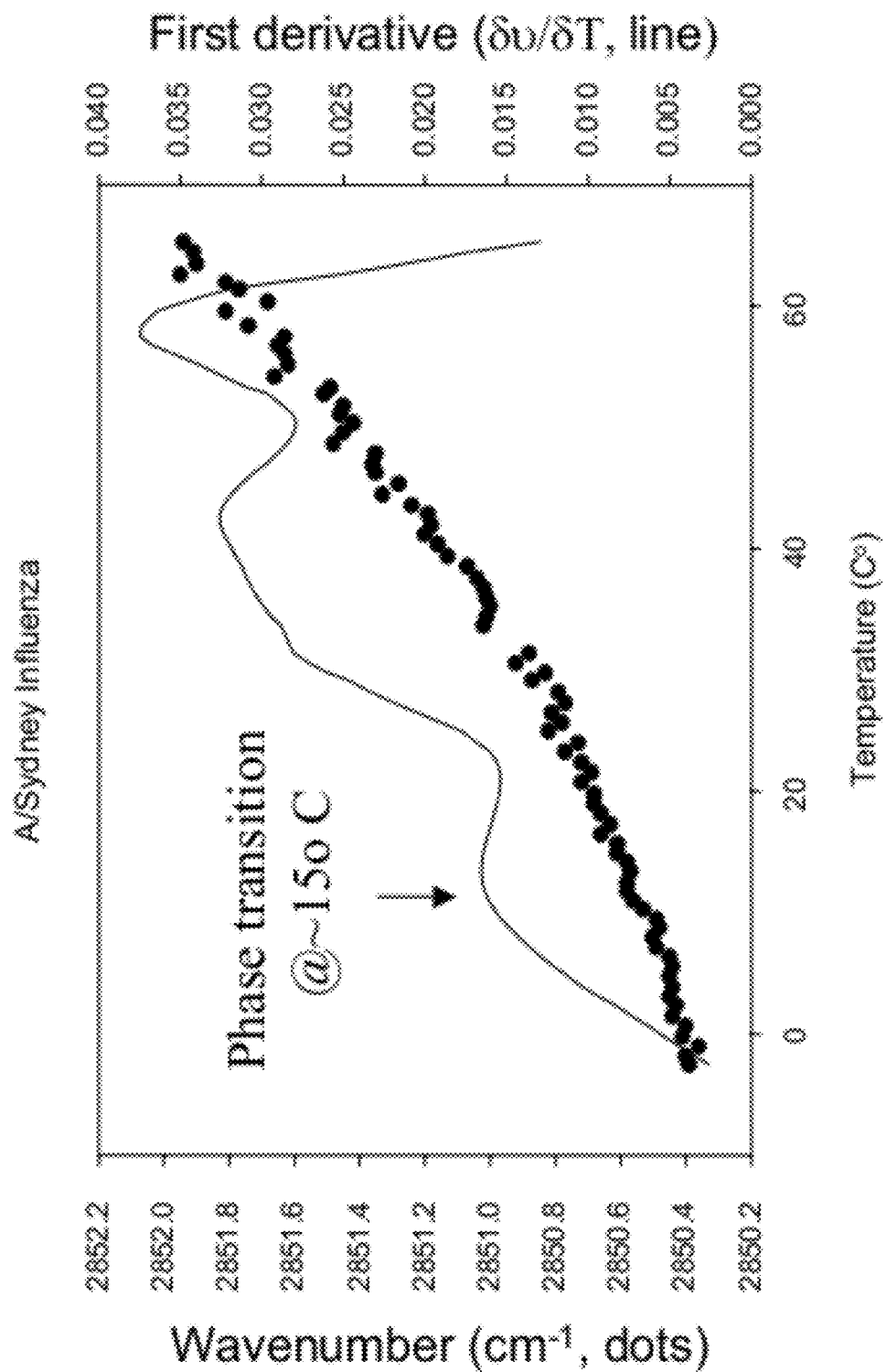
FIG. 3 shows the phase transitions of FluMist™ A/Sydney Influenza virus vaccine using Fourier transformed infrared spectroscopy (FTIR).

In one embodiment of the method, for example, the formulation includes a live attenuated influenza virus bioactive material in a solution of 40% sucrose, 5% gelatin, 0.02% Pluronic F68, and a pH 7.2 phosphate buffer. The formulation is aliquoted into sterile 10 ml siliconized glass vials and precooled to 15° C. (about the phase transition temperature of the virus membrane, see FIG. 3) for about 30 minutes. The pressure is rapidly reduced to about 50 mTorr for about an half an hour to generate the foam with ice nucleation and ice propagation throughout. After the initial foaming and freezing, ice sublimation and evaporation produce a physically stable foam. (such a foam can be generated at vacuums between about 400 Torr and 7.7 Torr or less, or 2.5 Torr to about 50 mTorr, when the formulation contains foaming agents). The temperature is increased to about 33° C. for about 2 days in a secondary drying step to reduce the residual moisture of the composition to a desired level. The vials are aseptically sealed to keep out contaminants and moisture for stability in storage.

Preparing a Formulation

Formulations of the invention can include, e.g., a bioactive material formulated into a solution or suspension containing a polyol, polymer, foaming agent, surfactant, and/or a buffer. The formulation ingredients can be combined in a sequence using techniques appropriate to the constituents, as is appreciated by those skilled in the art. For example, the polymers and/or high concentrations of polyols can be dissolved into a heated aqueous solution with agitation before cooling and admixture with the bioactive material. The bioactive material, such as a virus or bacterium, can be, e.g., concentrated and separated from growth media by centrifugation or filtration before resuspension into the formulation.

The bioactive material can be, e.g., a material of interest that provides any bioactivity, such as, e.g., enzymatic activity, storage of genetic information, an affinity interaction, induction of immune responses, cellular multiplication, infection, inhibition of cell growth, stimulation of cell growth, therapeutic effects, pharmacologic effects, antimicrobial effects, and/or the like. For example, the bioactive materials can be, enzymes, antibodies, hormones, nucleic acids, bacteria, viruses, liposomes, platelets, other cells, and/or the like. The bioactive material can be, e.g., living cells and/or viable viruses. The bioactive material can be, e.g., nonliving cells or liposomes useful as vaccines or delivery vehicles for therapeutic agents. Viral bioactive materials of the invention can be, e.g., live viruses such as, influenza virus, parainfluenza virus, AAV, adenovirus, respiratory syncytial virus, herpes simplex virus, cytomegalovirus, SARS virus, corona virus family members, human metapneumovirus, Epstein-Barr virus, and/or the like.

The protective agents of the methods can include, e.g., any of a variety of polyols. For example, the polyol, such as sucrose, can physically surround the bioactive material to promote retention of molecular structure throughout the drying process and impart structural rigidity to the glassy matrix in the dry state. Other functions of the polyol can include, e.g., protecting the bioactive material from exposure to damaging light, oxygen, moisture, and/or the like For example, the polyol, such as sucrose, can physically surround and protect the bioactive material from exposure to damaging light, oxygen, moisture, and/or the like. The polyols can, e.g., replace water of hydration lost during drying, to prevent denaturation of biomolecules of the material. In the methods of the invention, polyols can provide, e.g., a thickener with tenacity to foster formation and stabilization of bubbles that form the dry foam structure of the preservative compositions. Although the invention is not limited to any particular polyols, the formulation and foam compositions can include, e.g., sucrose, trehalose, sorbose, melezitose, sorbitol, stachyose, raffinose, fructose, mannose, maltose, lactose, arabinose, xylose, ribose, rhamnose, galactose, glucose, mannitol, xylitol, erythritol, threitol, sorbitol, glycerol, L-gluconate, and/or the like. Most polyols can be readily dissolved for mixture into the formulation in amounts ranging, e.g., from about 1 weight percent to about 45 weight percent, about 2 weight percent to about 40 weight percent, or about 5 weight percent to about 20 weight percent.

Polymers can be included in the formulations of the method, e.g., to provide protective benefits. As with polyols, polymers can provide, e.g., physical and chemical protection to the bioactive materials. The polymers can often provide, e.g., more thickening viscosity by weight to the formulation than simple polyols. The linear or branching strands of polymers can provide, e.g., increased structural strength to the dried foam compositions of the invention. Many polymers are, e.g., highly soluble in water, so they do not significantly hinder reconstitution of dry foams. Polymer protective agents, in the methods of the invention can include, e.g., hydrolyzed gelatin, unhydrolyzed gelatin, water soluble polymers such as polyvinyl pyrrolidone, ovalbumin, collagen, chondroitin sulfate, a sialated polysaccharide, actin, myosin, microtubules, dynein, kinetin, human serum albumin, and/or the like.

Foaming agents can be, e.g., formulation constituents capable of causing expansion of the formulation into a foam on application of reduced pressure. Foaming agents can be, e.g., small bubbles suspended in the formulation which can expand on application of reduced pressure and/or constituents capable of generating gas bubbles in the formulation. Foaming agents can be, e.g., gasses in solution, gas forming chemicals, readily boiling solvents, entrapped or suspended bubbles, injected bubbles, and/or the like.

Surfactants can be included in the formulations of the methods to provide, e.g., increased solubility to other formulation constituents, protection against surface tension induced denaturation of certain biomolecules during foaming, bubble stabilization, faster reconstitution, and/or the like. The surfactants can be, e.g., suitable ionic or non-ionic detergents, Tween surfactants, Pluronic surfactants, and/or the like.

Buffers can be added to the formulations of the method, e.g., to provide a suitable stable pH to the formulations of the method and compositions of the invention. Typical buffers of the invention include, e.g., potassium phosphate, sodium phosphate, sodium acetate, histidine, imidazole, sodium citrate, sodium succinate, ammonium bicarbonate, and/or a carbonate. The buffers can be adjusted to the appropriate acid and salt forms to provide, e.g., pH stability in the range from about pH 4 to about pH 10. A pH near neutral, such as, e.g., pH 7.2, is preferred for many compositions.

Other excipients can be included in the formulation. For example, amino acids, such as arginine and methionine can be constituents of the formulation and compositions. The amino acids can, e.g., act as zwitterions that block charged groups on processing surfaces and storage containers preventing non-specific binding of bioactive materials. The amino acids can increase the stability of compositions by, e.g., scavenging oxidation agents, scavenging deamidation agents, and stabilizing the conformations of proteins. In another example, glycerol can be included in the formulations of the invention, e.g., to act as a polyol and/or plasticizer in the dried foam composition. EDTA can be included in the composition, e.g., to scavenge metal ions that can initiate destructive free radical chemistries.

Cooling the Formulation

Formulations of the invention can be cooled before foam expansion, foam stabilization, freezing, and/or drying, to provide benefits, such as, e.g., stabilization of bioactivity, thickening of the formulation, enhanced penetration of formulation constituents through membranes, and/or freezing the formulation before lyophilization.

Cooling can be by any appropriate technique known in the art. For example, cooling can be by contact and conduction with refrigerated hardware, contact with streams of cold fluids, loss of latent heat, and/or the like. Typically, formulations are held in glass containers on racks within a temperature controlled process chamber where they equilibrate to the controlled temperature. The chamber can include, e.g., pressure control capabilities so that cooling can be driven by loss of latent heat from evaporation or sublimation of formulation solvents.

Figure 4:
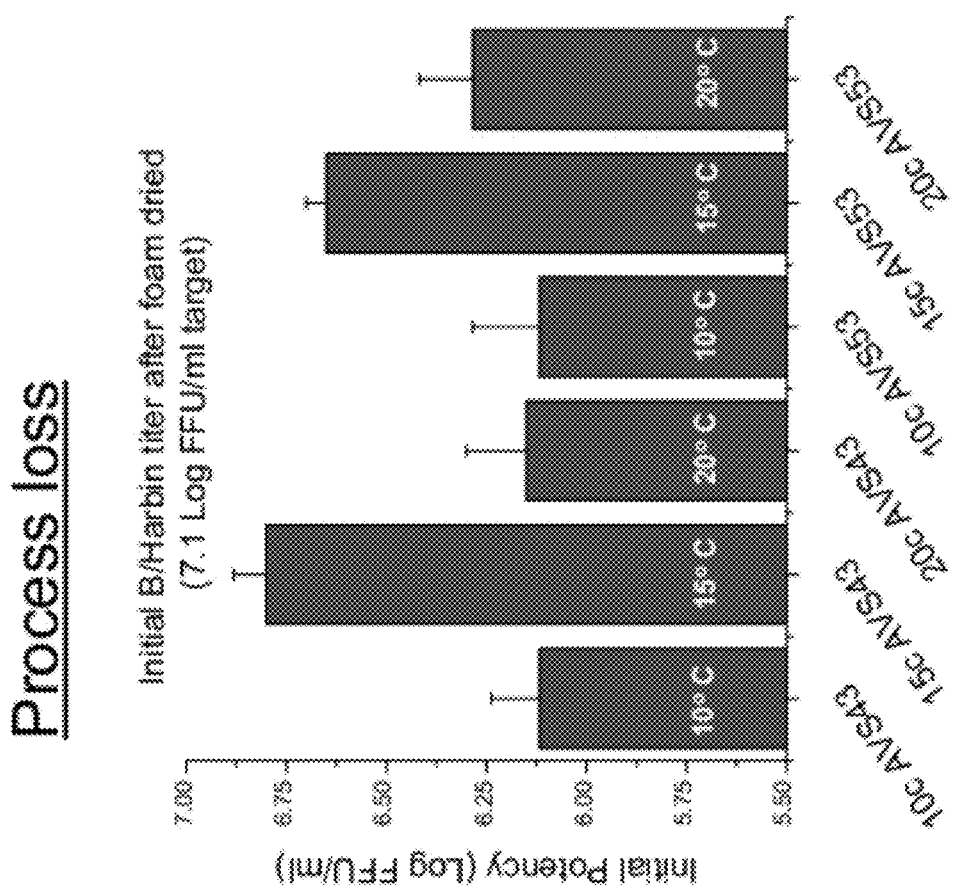
FIG. 4 shows process activity (viral titer) loss for B/Harbin influenza virus vaccine after the freeze dry foaming process where primary drying was conducted at 10° C., 15° C., and 20° C.
Figure 5:
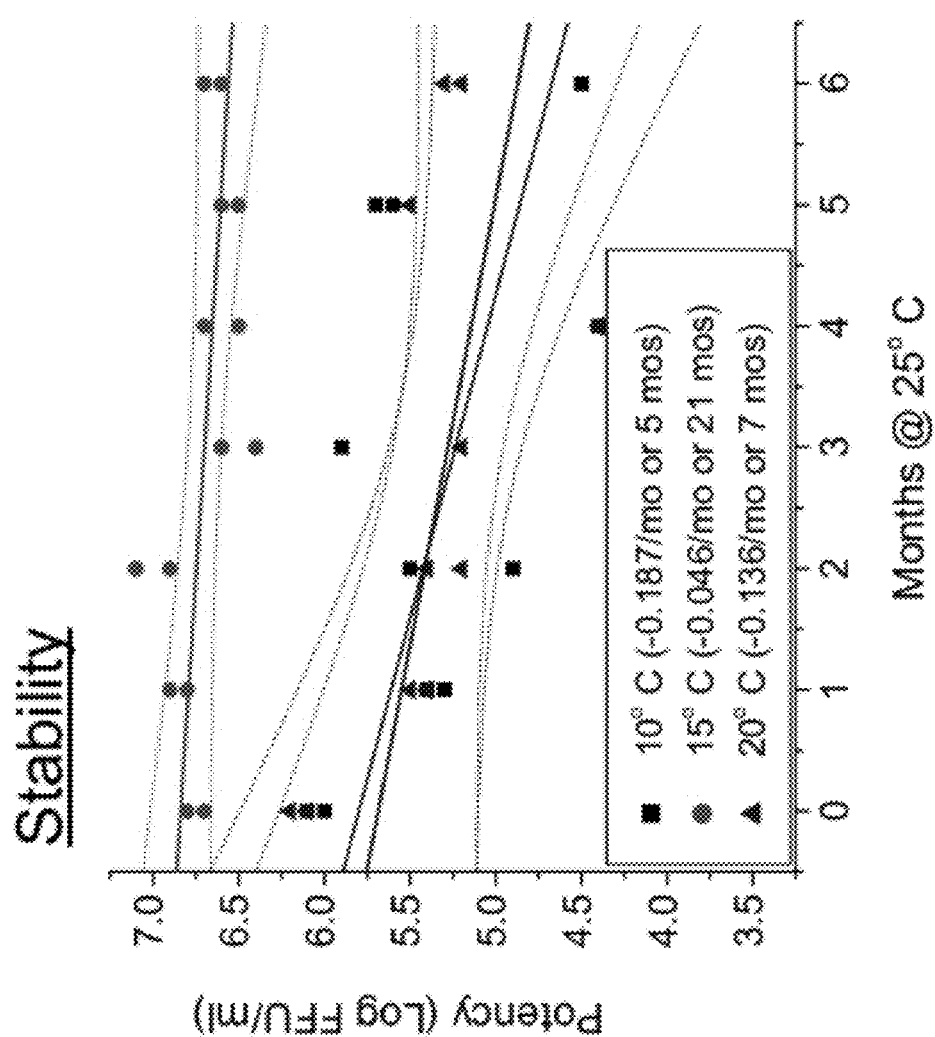
FIG. 5 shows the stability trend of B/Harbin influenza virus vaccine which was subjected to the freeze dry foaming process where primary drying was conducted at 10° C., 15° C., or 20° C.

The formulations of the invention can be, e.g., precooled to the phase transition temperature of biological material associated lipid membranes to enhance the penetration of protective agents. The lipid bilayers of biological membranes, and monolayers of some liposomes, can exist in a fluid phase at temperatures above the main phase transition temperature ($T_m$) and as a crystalline phase at temperatures below the $T_m$. Fluid phase membranes and crystalline phase membranes can present a continuous hydrophobic barrier to penetration by hydrophilic molecules. Without being bound to any particular theory, it is believed that at temperatures near the $T_m$, transmembrane defects can exist at the boundaries between regions of fluid and crystalline phases on a lipid membrane. Such transmembrane defects can provide increased permeability to hydrophilic molecules, such as many protective agents of the invention. Moreover, because the formulation has a high solids content, a chemical gradient is produced which further drives the solutes, such as protective agents, into the membrane. When moisture is later removed from the formulation, the protective agents can be retained within the membrane enclosed volume at stabilizing levels. Enhanced process stability and storage stability for virus exposed to protective agents at the membrane phase transition temperature (see, FIG. 3) are shown in FIGS. 4 and 5, respectively.

The $T_m$ of many lipid membranes is above the freezing temperature and the glass transition temperatures ($T_g$) of formulations of the invention. This allows ready diffusion of protective agents in liquid solution through lipid membranes at about their $T_m$. For example, a 40% solution of sucrose remains liquid for effective penetration of a cell at a typical membrane $T_m$ of 15° C. Increased permeability of protective agents in liquid solution through membranes in phase transition can protect biologic molecules within membrane enclosed volumes.

The $T_m$ of a membrane can be determined, e.g., Fourier Transformed Infrared (FTIR) microscopy, bending rigidity methods, ionic permeability studies, and the like. In methods of the invention, formulations of bioactive materials with lipid membranes can be held, e.g., at temperatures between about 0° C. to about 70° C., about 2° C. to about 45° C., about 12° C. to 16° C., or about 15° C. Live influenza virus foam dried at the putative phase transition temperature of 15° C. (see, FIG. 3) was found to be more resistant to process-related potency loss (see, FIG. 4) and exhibited significantly better long term stability at room temperature than that foam dried at 10° C. and 20° C. (see, FIG. 5). Formulations can be held at the $T_m$ to allow adequate penetration of protective agents. For example formulations can be held at the lipid membrane $T_m$ for about 10 to about 60 minutes, or about 30 minutes.

Foaming the Formulation

Foaming can result, e.g., from entrapment of gases released from the formulation and/or expansion of preexisting bubbles in suspension. For example, as gas pressure over the formulation is reduced, the boiling point of solvent constituents can drop below the temperature of the formulation, resulting in rapid evaporation or boiling of the solvent. Significant bubbling can also occur in the formulation, e.g., when the pressure is reduced below the partial pressure of gasses dissolved in the solvent, resulting in bubbles from degassing. Bubble formation can be chemically induced. Alternatively, bubbling can be physically induced by introducing a gas through the bottom of the vessel, e.g., such as through fritted glass.

Expanding the formulation into a foam can be by, e.g., expansion of bubbles within the formulation by reduction of applied pressure. The bubbles can be, e.g., preexisting, injected, and/or generated in situ. The bubbles can be, e.g., suspended within the formulation before expansion, injected into the formulation before or during expansion, or generated by boiling, degassing, or gas forming chemical reactions. Formulation constituents, e.g., included to promote expansion of the formulation into a foam can be foaming agents of the invention.

Expansion of the formulation can result, e.g., from boiling of the formulation. Boiling occurs, e.g., at the boiling point of a solvent, or when the vapor pressure of a formulation solvent exceeds the surrounding pressure. Boiling can be controlled, e.g., by adjusting the temperature of the formulation (higher temperatures result in higher vapor pressures) and/or by adjusting the applied pressure. Typically, formulations of the invention can be boiled under reduced pressure (vacuum, or pressure less than atmospheric) to provide a lowered boiling temperature more conducive to the stability of bioactive materials. Formulations comprising a solvent with a low boiling point (or high vapor pressure) can boil at lower temperatures. For example, inclusion of certain alcohols, ethers, fluorocarbons, and/or the like, can provide lowered boiling points for formulations of the invention.

Degassing can, e.g., provide expansion of the formulation into a foam. Gases can diffuse and dissolve into liquid solvents until an equilibrium is established between the partial pressures of gases in the liquid and the surrounding atmosphere. If the pressure of the surrounding atmosphere is, e.g., suddenly dropped, the gasses can rapidly escape the liquid as bubbles. For example, when an aqueous solution, which has been equilibrated with a gas at atmospheric pressure, is exposed to a lowered pressure, gas bubbles can form on the walls of the container or can erupt from the solution as a "fizz". This is not boiling, but is the release of dissolved gasses from the solution, or degassing. If the pressure is lowered further, the gasses can be substantially removed from the solution. Eventually, depending on the solvent, temperature and pressure, the solvent of the solution can begin to boil. Formulations of the invention can be expanded into foams under reduced pressure by degassing. Formulations can be exposed to gasses at suitable pressures, such as about one atmosphere (about 760 Torr at sea level) to about 500 atmospheres, to drive gasses into the formulation. Where the gas has equilibrated with the formulation at high pressures (greater than 1 atmosphere) the reduced pressure providing expansion does not have to be a vacuum (less than 1 atmosphere). Where the gas has equilibrated with the formulation at ambient pressures, or less, the reduced pressure initiating expansion of bubbles can be, e.g., a vacuum. Gasses that can act as foaming agents of the invention can be any known in the art, such as, air, nitric oxide, nitrogen, oxygen, low molecular weight hydrocarbons, inert gases, and/or the like.

Chemical reactions, e.g., which generate a gas can provide expansion of the formulation into a foam. Foaming agents of the invention can be, e.g., chemicals involved in gas generating chemical reactions, as will be appreciated by those skilled in the art. For example, a carbonate in the formulation can react with an acid to produce $CO_2$ gas. In other reactions, e.g., active metals, such as sodium or lithium, in the presence of water can react to provide hydrogen gas. Electrolytic reactions using direct electric currents can be used, e.g., to provide hydrogen and/or oxygen gasses at electrodes. Gasses generated within the formulation can, e.g., expand adiabatically or under constant pressure to expand the formulation into a foam. Optionally, gasses chemically generated within the formulation can be expanded by reduction of the applied pressure to expand the formulation into a foam.

Bubbles can be incorporated in to formulations, e.g., through mechanical processes. Formulations can be expanded into foam, e.g., by forceful incorporation of gas bubbles into the formulation and/or by expansion of injected small bubbles in a reduced pressure. For example, bubbles can be stirred, whipped, blown, jetted, agitated, sonicated, vortexed, blended, and/or the like, into the formulation. After introduction, e.g., into viscous formulations of the invention the bubbles can remain suspended for extended periods of time. Suspended bubbles can be, e.g., expanded by application of reduced pressure and/or stabilized by drying or cooling of the formulation. In one embodiment, small bubbles (e.g., 0.1 to 1 mm diameter) can be introduced into a formulation by the force of a pressurized gas through a filter membrane.

Foaming can be initiated or expanded by reducing pressure over the formulation. Foaming can be the result, e.g., from degassing of gasses from the formulation, expansion of small incorporated bubbles and/or boiling of the solvent. The escaping gasses can be trapped, e.g., by the viscous protective agents and/or surfactants of the formulation. The foaming step can result in, e.g., initial drying of the formulation, thickening and structural stabilization, and/or freezing of the foam.

Processes for preservation of bioactive materials comprising lipid membranes includes, e.g., a combination of precooling to a phase transition temperature and vacuum conditions that can result in freezing of the formulation. Because freezing can be a major cause of protein (and membrane damage) during freeze-drying, the prior art teaches the use of higher pressures (e.g., ~100 Torr or more), concentrated solutions, and/or higher initial temperatures to prevent freezing. The use of formulations containing various cryoprotective agents and process parameters of the invention can cryoprotect bioactive proteins and membranous should freezing result during the foam expansion, foam stabilization, or drying stages of the process.

Evaporation of solvent from the formulation can provide accelerated initial drying of the formulation under vacuum. The boiling of solvent speeds initial drying of the formulation, e.g., by rapid transfer of solvent out of the formulation, convective turn over of the formulation, and by increasing the surface area.

As evaporation proceeds, the foam structure can be stabilized. As solvent is driven from the formulation, the protective agents in solution can become concentrated and thick. Evaporation of solvent and loss of latent heat can cool the formulation. At some point, the cooled and concentrated protective agents can reach their glass transition temperature and stop flowing as a liquid. Loss of latent heat can result in freezing of the formulation. The glassy and/or frozen formulation can preserve a stable foam structure. An open cell foam structure can be provided throughout, e.g., by providing an etched glass bottom to the holding container to promote bubble formation at the bottom of the container. Bubbles traveling up through the thickening formulation can form interconnected spaces of an open cell foam. Open cell foam can also be promoted by rapid drying and thickening that prevents settling of bubble free formulation or formation of a sealing skin over the formulation. Open cell foam can shorten secondary drying times and reconstitution times.

Foaming can be affected by conditions, such as, e.g., types and concentrations of formulation constituents, formulation temperatures, applied pressure levels, the rate of pressure changes, and/or the like. For example, the presence of surfactants or thickening agents can stabilize bubbles for a less dense foam. In another example, replacement of lost latent heat, e.g., by heating the process chamber, can prolong the boiling of solvent. In another example, lower pressures can provide more vigorous or continuous boiling. Pressure can be reduced, e.g., to less than about 400 Torr, about 200 Torr or less, between about 100 Torr and about 25 Torr or less, between 25 Torr and 7.7 Torr or less, or between 2500 mTorr and about 50 mTorr, or about 25 mTorr or less, to produce desired foaming and/or freezing in the methods of the invention. The vacuum can be maintained for about 1 hour or about 2 hours, e.g., to complete foaming, foam stabilization, and initial drying of the foam.

Initial (primary) drying in the methods of the invention can include, e.g., lyophilization. When latent heat is lost without replacement, e.g., the freezing temperature of the formulation can be reached. As additional latent heat is lost due to evaporation and/or sublimation, the formulation can freeze, e.g., stabilizing a foam structure. Initial drying can continue, e.g., as additional solvent is removed by sublimation into the vacuum. The sublimation and/or evaporation can be driven, e.g., by removal of solvent (moisture) from the gaseous environment around the foam by condensation or desiccation.

Secondary Drying

Secondary drying of the structurally stabilized and initially dried foam can, e.g., remove entrapped solvent, or water of molecular hydration, to provide a composition that is stable in storage, e.g., for extended periods at ambient temperatures. Secondary drying can involve, e.g., application of warm temperatures in a strong vacuum for several hours to days.

For example, heat can be added to the initially dried foam to drive off residual solvent. Heat can be applied, e.g., through heating the reduced pressure atmosphere and/or heat can be conducted to the foam through associated hardware, such as shelves, trays, and glass vials. The drying temperature can be, e.g., less than the glass transition temperature of the remaining composition in order to prevent collapse of the foam structure. The methods of the invention result in a pharmaceutically-acceptable, glassy matrix comprising at least one biologically active material within the amorphous glassy matrix. Preferably, the composition is almost completely dry. Some water or other aqueous solvent can remain in the composition but typically, not more than 10% residual moisture remains by weight. The drying temperature can range from about 10° C. to about 70° C., about 25° C. to about 45° C., or about 35° C. A typical secondary drying process can include, e.g., raising the temperature to a drying temperature of from about 30° C. to about 35° C., and holding for from about 0.5 days to about 5 days to provide a stable dried foam composition with 0.1% to about 10%, or about 3% residual moisture. As used herein, "dry", "dried", and "substantially dried" encompass those compositions with from about 0% to about 5% water. Preferably, the glassy matrix will have a moisture content from about 0.1% to about 3% as measured using the Karl Fisher method.

A vacuum can be provided in the secondary drying process to drive the rate of water removal and/or to push removal to lower residual moisture levels. The vacuum during secondary drying can be, e.g., less than 400 Torr, less than 100 Torr, less than 2.5 Torr, less than 500 mTorr, less than 100 mTorr, less than 50 mTorr, or preferably about 25 mTorr.

Figure 8:
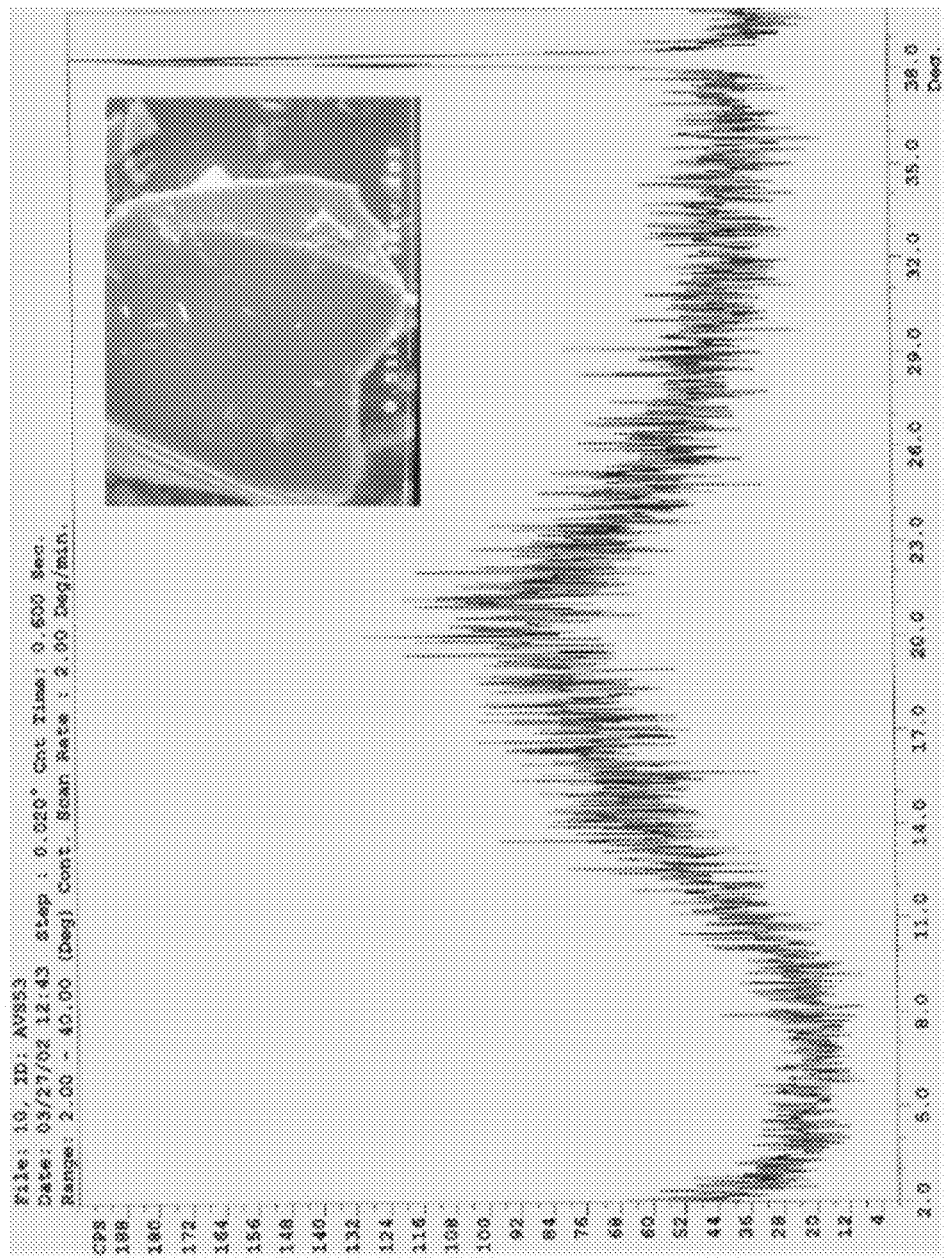
FIG. 8 shows X-ray diffraction data and an electron micrograph demonstrating the amorphous nature of a foam composition of the invention.

The resulting product from this process is generally an amorphous solid (see, FIG. 8), wherein the glassy excipient material, e.g. sucrose, is in an amorphous glassy state and encases the biologically active material, thereby preventing protein unfolding and significantly slowing molecular interactions or cross-reactivity, due to greatly reduced mobility of the compound and other molecules within the glassy composition. This process has been postulated to occur either via mechanical immobilization of the protein by the amorphous glass or via hydrogen bonding to polar and charged groups on the protein, i.e. via water replacement, thereby preventing drying induced denaturation and inhibiting further degradative interactions. As long as the glassy solid is at a temperature below its glass transition temperature and the residual moisture remaining in the excipients is relatively low, the labile proteins and/or bioactive material containing lipid membranes can remain relatively stable. It should be noted that achieving a glassy state is not necessarily a prerequisite for long term stability as some active ingredients may fare better in a more crystalline state. While it is generally recognized that biomaterials are generally easier to stabilize when dried to an amorphous glassy state, there are cases where the such glassy state is neither necessary nor sufficient for long term preservation. It is important to note that the mechanisms attributed to stabilization of biologicals can be multifactorial and not limited to the amorphous nature of the powder matrix in which the active ingredient is encased. Stabilization under the process described here can involve a number of factors including but not limited to the reduction in conformational mobility and flexibility of the protein side chains and/or reduction in the free volume as a result of the encasement, improvement in the structural rigidity of the matrix, reduction in the phase separation of excipient from the active ingredient, improvement in the degree of water displacement by selecting the optimal hydrogen bonding donor. The latter is a function of the affinity and avidity of the excipient for the surface of the protein, nucleic acids, carbohydrate, or lipids being stabilized. In general, as long as the solid is at a temperature below its glass transition temperature and the residual moisture remaining in the excipients is relatively low, the labile proteins and/or bioactive material containing lipid membranes can remain relatively stable.

Filling and Administration

Formulations can be, e.g., filled into containers before foaming and drying, or aliquoted into individual containers for use, as desired. Formulations can be filled, e.g., into standard glass lyophilization vials for processing into stabilized foams. The glass vials can be sterile with an etched bottom and a hermetically sealable stopper. Bioactive materials of the invention can be administered, e.g., by injection of reconstituted solutions or suspensions, or inhalation of ground foam powder particles.

Figure 6:
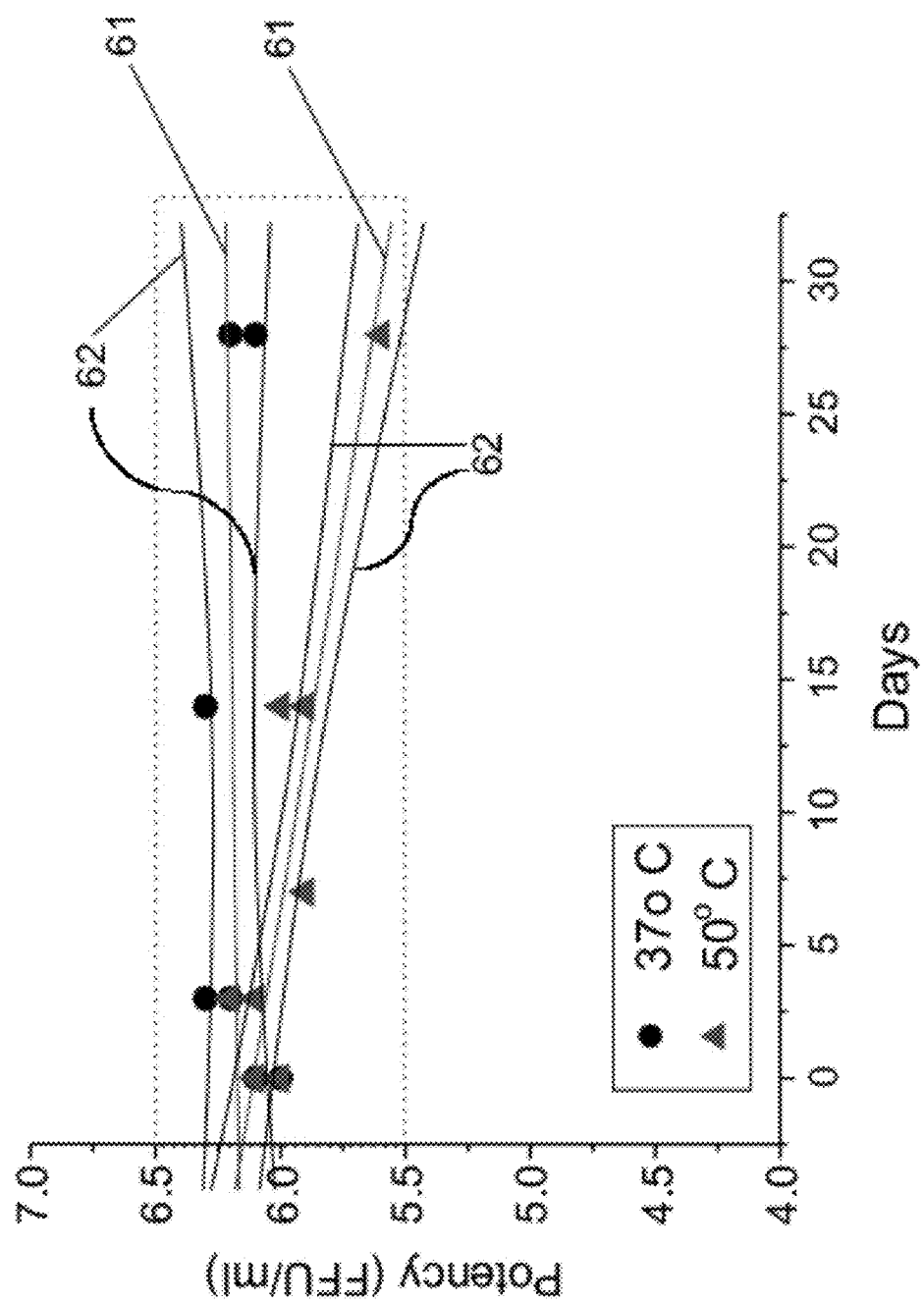
FIG. 6 shows the stability trend for potency of foam dried B/Ann Arbor influenza virus in storage at 37° C. and 50° C.
Figure 7:
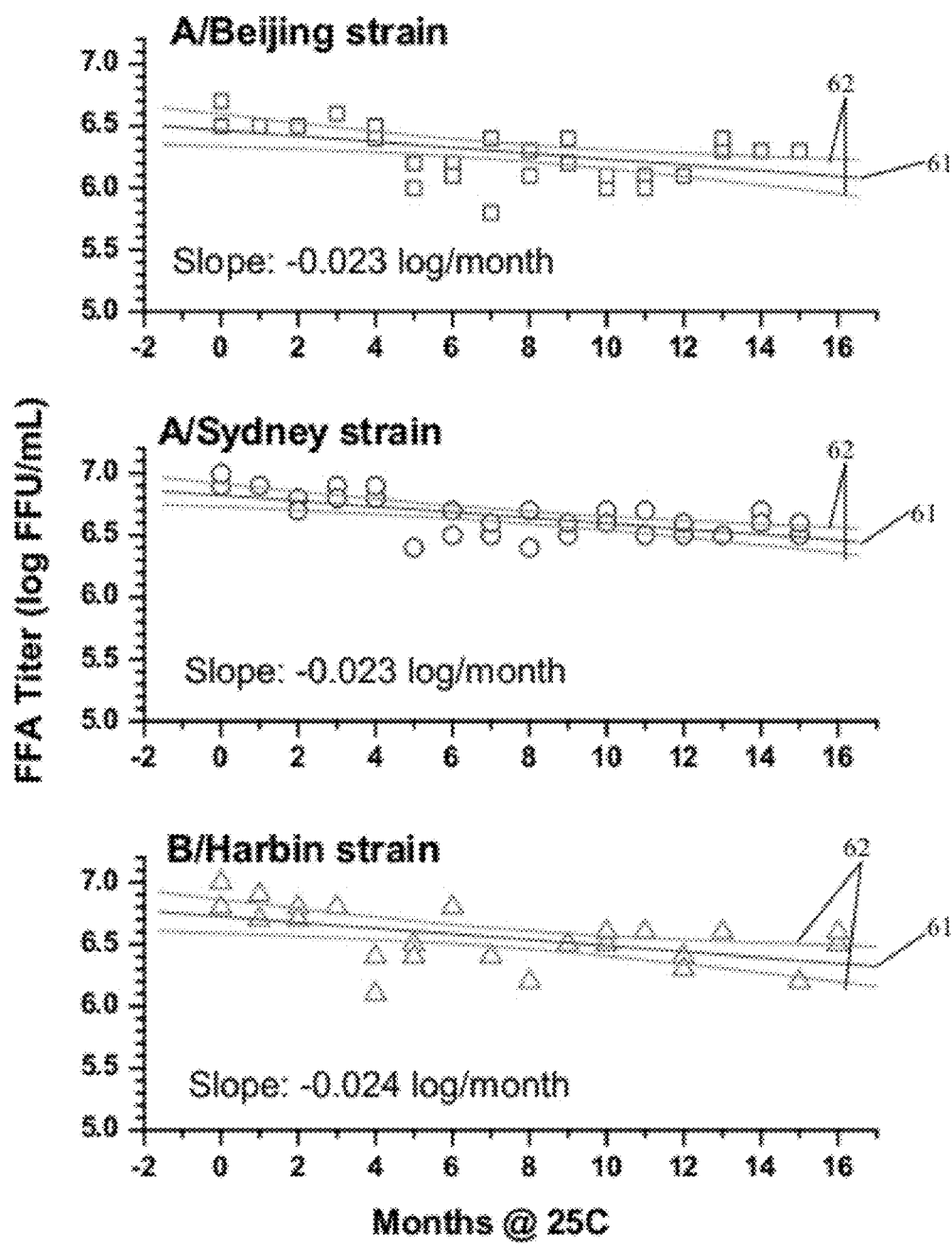
FIG. 7 shows the stability trends for three different strains of influenza virus vaccine foam dried in formulation AVS53.

The compositions described herein can be stable, i.e., they preserve the biological activity of the encased biologically active material and are chemically and/or physically stable. The compositions were tested for stability by subjecting them to aging at elevated temperature (e.g., 37° C.) and measuring the biological activity, chemical and/or physical stability of the formulations. As an example for live attenuated influenza virus vaccine (FluMist™), results of these studies demonstrate that the virus formulated in these formulations were stable for at least one month at 50° C. and for more than three months at 37° C. (see, FIG. 6). Stability is defined as time for one log fluorescent focus unit/ml (FFU/ml) potency loss. At 25° C., the live influenza viruses were stabile for more than one year (see, FIG. 7). Such formulations are stable even when high concentrations of the biologically active material are used. Thus, these formulations are advantageous in that they may be shipped and stored at temperatures at or above room temperature for long periods of time.

The stable composition of the bioactive material in an amorphous glassy matrix (see, FIG. 8) provided after drying can be further processed using methods known in the art. For example, the glass matrix is easily divisible by cutting, milling, or other dividing techniques. Processes for grinding or pulverizing drugs are well known in the art. For example, a hammer mill, an impact mill known as Entoleter mill, a jet mill, a pin mill, a Wiley mill, or similar milling device can be used. The preferred particle size is less than about 100 um to about 0.1 um, and preferably less than 50 um. Particles less than about 10 um in size are suitable, e.g., for pulmonary administration by inhalation, while larger particles can be suitable for administration to the upper respiratory tract and nasal regions. The particle size can be chosen so as to obtain varying dispersion and flowability characteristics. For example, free flowing powders may be especially desirable for intranasal or pulmonary delivery. The powdered compositions of the invention can be easily rehydrated with water, saline, or other fluids.

Dry foam compositions can be reconstituted with a suitable aqueous buffer for administration by injection or inhalation.

For example, compositions of the invention can be administered to a mammal by delivering the bioactive material through the intravenous, intramuscular, intraperitoneal, intracerebrospinal, subcutaneous, intra-articular, intrasynovial, intrathecal, oral, topical, intranasal, or pulmonary routes. The large surface area of foam and the high solubility of many protective agents allows dry foams of the invention to be reconstituted at lower or higher concentrations than the original formulation. In some cases, e.g., the bioactive material can be reconstituted at high concentrations, such as up to about 400 mg/ml, for delivery of an adequate dose in a small volume subcutaneous injection. Less concentrated reconstituted solutions can be, e.g., administered as an aerosol by inhalation. The choice of administration route can depend on, e.g., the site of action, pharmacological considerations, and the like. A typical dose of a bioactive material in the methods of the invention is from about 0.01 ng/kg to about 15 mg/kg.

The appropriate dosage ("therapeutically effective amount") of the biologically active material will depend, for example, on the condition to be treated, the severity and course of the condition, whether the biologically active material is administered for preventive or therapeutic purposes, previous therapy, the patient's clinical history and response to the biologically active material, the type of biologically active material used, and the discretion of the attending physician. The biologically active material can be suitably administered to the patent at one time, or over a series of treatments, and may be administered to the patent at any time from diagnosis onwards. The biologically active material may be administered as the sole treatment or in conjunction with other drugs or therapies useful in treating the condition in question.

As a general proposition, the therapeutically effective amount of the biologically active material administered will be in the range of about 0.01 ng/kg to about 50 mg/kg of patent body weight whether by one or more administrations, with the typical range of protein used being about 0.05 ng/kg to about 20 mg/kg, more preferably about 0.1 ng/kg to about 15 mg/kg, administered daily, for example. However, other dosage regimens may be useful. The progress of this therapy can be monitored by conventional techniques.

In another embodiment of the invention, an article of manufacture is provided comprising a container which holds the pharmaceutical compositions of the present invention and optionally provides instructions for its use. Suitable containers include, for example, bottles, vials and syringes. The container may be formed from a variety of materials such as glass or plastic. An exemplary container is a 3-20 cc single use glass vial. Alternatively, for a multidose formulation, the container may be 3-100 cc glass vial. The container holds the formulation and the label on, or associated with, the container may indicate directions for use. The article of manufacture may further include other materials desirable from a commercial and user standpoint, including other buffers, diluents, filters, needles, syringes, and package inserts with instructions for use.

Compositions of the Invention

Compositions of the invention include dry foam compositions of a bioactive material and a polyol and/or a polymer. Compositions of the invention can be prepared, e.g., by the methods of the invention. Compositions of the invention can be prepared by, e.g., preparing a formulation of a polyol and a bioactive material with lipid membranes, cooling the formulation to a temperature of about a phase transition temperature of the lipid membranes, reducing pressure on the formulation to form a foam, freezing the foam, and sublimating water from the frozen foam to provide a lyophilized dry foam composition. Secondary drying conditions can be employed to further dry the foam. Compositions of the invention include, e.g., reconstituted dry foam in an aqueous buffer.

In one embodiment, the composition of the invention is a vaccine of live attenuated influenza virus. The composition is prepared, e.g., according to the methods of the invention including secondary drying the foam at a drying temperature below the glass transition, e.g., between 30° C. and 35° C., for between 6 hours and 5 days, to provide a final composition with less than about 5% residual moisture. Such a composition can remain stable in storage at about 25° C. for 1 year or more.

FIGS. 5 and 6 show charts of stability data for an envelope virus preserved in the dry foam of the invention and stored at 25° C., 37° C., and 50° C. The charts of potency (fluorescent focus units per mL—FFU/mL) versus time with individual data time-points as dots or squares. Trend lines 51 and 95% confidence intervals 52 indicate a predicted stability (not more than 1 log potency loss) of about 40 months for virus stored in the composition of the invention at 25° C.

In another embodiment, the compositions of the invention include, e.g., blood platelets preserved in stable storage as bioactive material in a dry foam. Blood platelets are cytoplasmic fragments from megakaryocytes that can aggregate at the site of blood vessel lesions to prevent bleeding and initiate repairs. Platelet infusions into patients are used to correct deficiencies or dysfunctions of circulating platelets as a result of trauma, disease, or drug induced dysfunction. For example, patients suffering from idiopathic thrombocytopenia, sickle cell anemia, and those undergoing ablative chemotherapy can be treated with platelet infusions. The increasing use of ablative chemotherapy for a wide variety of malignancies has resulted in an increased need for replacement platelet therapy. A major difficulty in using isolated platelets is their short shelf-life. Platelets are only approved by the Food and Drug Administration (FDA) for storage in a liquid state for up to five days at room temperature, during which time the functional properties rapidly deteriorate. This causes many logistic problems in both civilian and military medicine.

Compositions for preservation of platelets can be prepared by collecting blood into a suitable anticoagulant followed by obtaining platelet rich plasma (PRP) by any method known in the art. The platelets can be processed according to the methods of the invention to yield a stable dried foam comprising the platelets. Because platelets are large and more complex structure than a virus, drying at its characteristic phase transition is particularly important. The dried platelets can be reconstituted by resuspension in a physiologically acceptable buffer before infusion. For therapeutic use, the buffer is sterile. The buffer can be any buffer of suitable pH. Preferably, the reconstitution buffer can contain a substance or substances that exhibit high colloidal osmotic pressure, including, but not limited to, polyethylene glycol (PEG) and hydroxy-ethyl starch (HES). Preferably, the buffer is 1-5% human serum albumin (HSA) in saline.

Formulations for Preparation of Dry Foam Compositions

Formulations for preparation of dry foam compositions of the invention can include, e.g., bioactive materials, polymers, polyols, foaming agents, surfactants, and/or buffers. Such formulations can be processed according to methods of the invention to provide stable compositions for storage and administration of the bioactive materials.

Bioactive materials of the invention include, e.g., materials with detectable bioactivity in living systems, biological cells and molecules used in analysis, biological cells and molecules used in medicine, biological cells and molecules used in research, and/or the like. For example, bioactive materials of the compositions of the invention include peptides, proteins, hormones, nucleic acids, antibodies, vaccines, bacteria, viruses, liposomes, platelets, cell suspensions, and/or the like.

Bioactive materials comprising lipid membranes in the compositions are generally live, biologically active, viable or non-living, cells, viruses, and/or liposomes. For example the bioactive agents can include vaccines, viruses, liposomes, bacteria, platelets, and cells. Viral bioactive agents can include, e.g., influenza virus, parainfluenza virus, AAV, adenovirus, respiratory syncytial virus, herpes simplex virus, SARS virus, human metapnuemovirus, corona virus family members, cytomegalovirus, and/or Epstein-Ban virus which can be present in the formulations of the invention in amounts ranging from about $10^1$ $TCID_{50}$/mL or more, from about $10^3$ $TCID_{50}$/mL up to about $10^{12}$ $TCID_{50}$/mL, or from about $10^6$ $TCID_{50}$/mL to about $10^9$ $TCID_{50}$/mL. The bioactive material will generally be present in an amount of less than about 1%; more preferably, less than about 0.001%; and most preferably, less than about 0.0001% by weight.

The formulations for preparation of dry foam compositions can include, e.g., substantial total solids (constituents minus the solvent, such as water). A major portion of the total solids can comprise the bioactive material, a polyol, and/or a polymer. For example, the polyol can be present in the formulation in a concentration ranging from about 2 weight percent to about 50 weight percent, from about 5 weight percent to about 45 weight percent, or from about 20 weight percent to about 40 weight percent. In another example, the polymer can be present in the formulation in a concentration ranging from about 1 weight percent to about 10 weight percent, or about 5 weight percent. Preferably, the formulation should have a high solids content, typically between about 5% and 70%, or between about 30% to 50%. The viscosity of formulations of the invention are typically greater than 5 centipoise (cP); more preferably, greater than 10 cP. A preferred formulation exhibits ~12 cP.

Polyols of the invention can include, e.g., various sugars, carbohydrates, and alcohols. For example, the polyols can include non-reducing sugars, sucrose, trehalose, sorbose, melezitose, and/or raffinose. The polyols can include, e.g., mannose, maltose, lactose, arabinose, xylose, ribose, rhamnose, galactose and glucose, mannitol, xylitol, erythritol, threitol, sorbitol, glycerol, or L-gluconate. Where it is desired that the formulation be freeze-thaw stable, the polyol is preferably one which does not crystallize at freezing temperatures (e.g. −20° C.) such that it destabilizes the biologically active material in the formulation.

Polymers of the invention can include, e.g., various carbohydrates, polypeptides, linear and branched chain hydrophilic molecules. For example, polymers of the formulation can include gelatin, hydrolyzed gelatin, ovalbumin, polyvinylpyrrolidone, collagen, chondroitin sulfate, a sialated polysaccharide, actin, myosin, microtubules, dynein, kinetin, or human serum albumin. These additives do not necessarily solely stabilize the biologically active material against inactivation; they also may help to prevent the physical collapse of the freeze-dried material during lyophilization and subsequent storage in the solid state. Other gelatin substitutes that may also function as stabilizers include native collagen and alginate.

Preferably, gelatin and more preferably, hydrolyzed gelatin, is used. "Hydrolyzed gelatin" refers to gelatin that has been subjected to partial hydrolysis to yield a partially hydrolyzed gelatin having a molecular weight of from about 1 kDa to about 50 kDa, or about 3 kDa. This gelatin hydrolysis product has approximately the same amino acid composition as gelatin. The typical amino acid composition of hydrolyzed gelatin is known. Partially hydrolyzed gelatin may be obtained from any number of commercial sources. Partially hydrolyzed gelatin may also be obtained by enzymatic hydrolysis of gelatin by means of a proteolytic enzyme, such as, for example, papain, chymopapain, and bromelin, although other known hydrolysis means may be employed, e.g., acid hydrolysis. Preferably, a gelatin having a molecular weight of between about 1 kDa and 50 kDa is used. Gelatin hydrolyzed to about 3 kDa or less can be less allergenic than full length gelatin. The gelatin may be derived from a variety of sources, including pig and bovine. Humanized collagen as well as highly processed collagen, for example, FreAlagin, a pharmaceutical gelatin with reduced allergenicity, available from Miyagi Chemical Industrial Co, Ltd., can be used. Again, the amount of gelatin used in the formulation will vary depending on the overall composition of the formulation and its intended use. Generally, the concentration of gelatin will be from about 1 to about 7%; more preferably, between about 1 and 5%. A preferred formulation comprises about 5% gelatin.

Formulations for preparation of the compositions of the invention can include, e.g., one or more surfactants to aid in solubility and stability of formulation constituents. The surfactants can include, e.g., nonionic detergents, such as polyethylene glycol sorbitan monolaurate (Tween 20), polyoxyethylenesorbitan monooleate (Tween 80), block copolymers of polyethylene and polypropylene glycol (Pluronic), and/or the like. The formulations can include ionic detergents. Formulations and compositions of the invention can include surfactants, such as, e.g., polyethylene glycol, polypropylene glycol, polyethylene glycol/polypropylene glycol block copolymers, polyethylene glycol alkyl ethers, polypropylene glycol alkyl ethers, polyethylene glycol/polypropylene glycol ether block copolymers, alkylarylsulfonates, phenylsulfonates, alkyl sulfates, alkyl sulfonates, alkyl ether sulfates, alkyl aryl ether sulfates, alkyl polyglycol ether phosphates, polyaryl phenyl ether phosphates, alkylsulfosuccinates, olefin sulfonates, paraffin sulfonates, petroleum sulfonates, taurides, sarcosides, fatty acids, alkylnaphthalenesulfonic acids, naphthalenesulfonic acids, lignosulfonic acids, condensates of sulfonated naphthalenes with formaldehyde, or condensates of sulfonated naphthalenes with formaldehyde and phenol, lignin-sulfite waste liquor, alkyl phosphates, quaternary ammonium compounds, amine oxides, betaines, and/or the like. Surfactants can be present in formulations of the invention in a concentration ranging from about 0.001 weight percent to about 2 weight percent, or about 0.01 weight percent to about 1 weight percent.

Buffers can be present, e.g., to control pH, enhance stability, affect constituent solubility, provide comfort on administration, and the like, in formulations for preparation of dry foam compositions. Formulation pH can be controlled in the range of about pH 4 to about pH 10, from about pH 6 to about pH 8, or about pH 7.2. Preferred buffers are often paired acid and salt forms of a buffer anion generally recognized as safe for the particular route of administration of the bioactive material. Typical buffers for use in the formulations and compositions of the invention include, e.g., potassium phosphate, sodium phosphate, sodium acetate, sodium citrate, histidine, imidazole, sodium, succinate, ammonium bicarbonate, carbonates, and the like.

In one embodiment, the formulation contains the above-identified agents (i.e., biologically active material, polyol, surfactant, and gelatin) and is essentially free of one or more preservatives, such as benzyl alcohol, phenoly, m-cresol, chlorobutanol, and benethonium chloride). In another embodiment, a preservative may be included in the formulation, particularly when the formulation is a multidose formulation.

One or more pharmaceutically acceptable carriers, excipients, or stabilizers such as those described in Remington's Pharmaceutical Sciences 16$^{th}$ Edition, Osol, A. Ed. (1980) may be included in the formulation provided that they do not adversely affect the desired characteristics of the formulation. Acceptable carriers, excipients or stabilizers are nontoxic to recipients at the dosages and concentrations employed and include; additional buffering agents; co-solvents; salt-forming counterions such as potassium and sodium; antioxidants, such as methionine, N-acteyl cysteine, or ascorbic acid; chelating agents, such as EDTA or EGTA. Amino acids, such as, e.g., arginine and methionine can be included in the formulations. Arginine can be present in the formulations in an amount ranging from about 0.1 weight percent to about 5 weight percent. Methionine can be present in the formulation in a concentration ranging from about 1 mM to about 50 mM or about 10 mM. Glycerol can be present in the formulation in a concentration ranging, e.g., from about 0.1 weight percent to about 5 weight percent, or about 1 weight percent. EDTA can be present in the formulation in a concentration ranging, e.g., from about 1 mM to about 10 mM, or about 5 mM.

EXAMPLES

The following examples are offered to illustrate, but not to limit the claimed invention.

Example 1

Preservation of Live Attenuated Virus

This example describes a composition that maintained protein integrity and stability after storage at 37° C. for 125 days.

Monovalent live attenuated influenza virusB/Harbin (CAZ039 lot) was formulated as an 8.0 log FFU/ml titer solution (~10 microgram/ml total protein concentration of viral stock solution) containing 40% sucrose, 5% gelatin, 0.02% Pluronic F68, 25 mM 7.2 pH KP0$_4$ buffer. One mL aliquots of this solution were then dispensed into 10 mL glass lyophilization vials, partially covered with lyophilization stoppers, and lyophilized using a VirTis Genesis 25EL lyophilizer (available from VirTis, Gardiner, N.Y.) according to the following cycle conditions:

1) Pre-cool shelves to 15° C. (with desiccant on lyophilizer shelf with the condenser set at −60° C.);

2) Load vials and allow to equilibrate for 30 minutes;

3) Set vacuum to 50 mTorr;

4) Hold for 60 minutes;

5) Ramp to 33° C. at about 0.7° C./minute;

6) Hold for 48 hours; and

7) Stopper vials.

The resultant foam had a moisture content of approximately 2.2% (w/w) and a $T_g$ of about 43° C.

Example 2

Formulations

The following formulations were prepared according to the methods of this invention using B/Harbin influenza virus or placebo. The pH of formulations were adjusted with either sodium hydroxide or potassium hydroxide.

| ID | Glutamate | Polyol | Polymer Additive | Surfactant | Other |
|---|---|---|---|---|---|
| AVS1 | 20% | 10% sucrose | 5% Gelatin | 0.1% Pluronic F68 | 2% arginine, 5 mM EDTA, 10 mM methionine, 50 mM 7.2 KPO4 buffer |
| AVS2 | 20% | 10% sucrose | — | 0.1% Pluronic F68 | 5% arginine, 5 mM EDTA, 10 mM methionine, 7.2 KPO4 buffer 50 mM, |
| AVS3 | 25% | 15% sucrose | — | 0.1% Pluronic F68 | 5% arginine, 5 mM EDTA, 50 mM 7.2 KPO4 buffer |
| AVS4 | 25% | 15% sucrose | — | 0.1% Pluronic F68 | 5% arginine, 50 mM 7.2 KPO4 buffer |
| AVS5 | 25% | 5% sucrose | — | 0.1% Pluronic F68 | 5% arginine, 50 mM 7.2 KPO4 buffer |
| AVS1A | 20 | 10% sucrose | 5% Gelatin | 0.1% Pluronic F68 | 2% arginine, 5 mM EDTA, 10 mM methionine, 50 mM 7.2 KPO4 buffer |
| AVS2A | 20 | 10% sucrose | | 0.1% Pluronic F68 | 5% arginine, 5 mM EDTA, 10 mM methionine, 50 mM 7.2 KPO4 buffer |
| AVS3A | 25 | 15% sucrose | | 0.1% Pluronic F68 | 5% arginine, 5 mM EDTA, 10 mM methionine, 50 mM 7.2 KPO4 buffer |
| AVS4A | 25 | 15% sucrose | | 0.1% Pluronic F68 | 5% arginine, 50 mM 7.2 KPO4 buffer |
| AVS5A | 25 | 5% sucrose | | 0.1% Pluronic F68 | 5% arginine, 50 mM 7.2 KPO4 buffer |
| AVS6 | 20 | 10% sucrose | 5% Gelatin | 0.1% Pluronic F68 | 2% arginine, 5 mM EDTA, 10 mM methionine |

-continued

| ID | Glutamate | Polyol | Polymer Additive | Surfactant | Other |
|---|---|---|---|---|---|
| AVS7 | 20 | 10% sucrose | | 0.1% Pluronic F68 | 5% arginine, 5 mM EDTA, 10 mM methionine, 50 mM 7.2 KPO4 buffer |
| AVS8 | 25 | 15% sucrose | | 0.1% Pluronic F68 | 5% arginine, 5 mM EDTA, 10 mM methionine, 50 mM 7.2 KPO4 buffer |
| AVS9 | 25 | 15% sucrose | | 0.1% Pluronic F68 | 5% arginine, 50 mM 7.2 KPO4 buffer |
| AVS10 | 25 | 5% sucrose | | 0.1% Pluronic F68 | 5% arginine, 50 mM 7.2 KPO4 buffer |
| AVS11 | 10% | 20% sucrose; 10% raffinose | | 0.2% Pluronic F68 | 1% arginine, 50 mM 7.2 KPO4 buffer |
| AVS12 | 20 | 20% raffinose | | 0.2% Pluronic F68 | 1% arginine, 50 mM 7.2 KPO4 buffer |
| AVS13 | 25 | 10% sucrose; 2% raffinose | | 0.2% Pluronic F68 | 5% arginine, 50 mM 7.2 KPO4 buffer |
| AVS14 | 20 | 10% sucrose | | 0.2% Pluronic F68 | 10 mM methionine, 50 mM 7.2 KPO4 buffer |
| AVS15 | 20 | 10% sucrose | 1% Gelatin | 0.2% Pluronic F68 | 10 mM methionine |
| AVS16 | 20 | 10% sucrose | 1% Gelatin | 0.2% Pluronic F68 | 10 mM methionine |
| AVS17 | 20 | 2% raffinose | 1% Gelatin | 0.2% Pluronic F68 | 10 mM methionine, |
| AVS18 | 20 | 10% raffinose | | 0.2% Pluronic F68 | 10 mM methionine |
| AVS19 | 20 | 10% sucrose | | 0.2% Pluronic F68 | 10 mM methionine, 100 mM 7.0 citrate buffer |
| AVS20 | 20 | 10% sucrose | 1% Gelatin | 0.2% Pluronic F68 | 10 mM methionine, 100 mM 7.0 citrate buffer |
| AVS21 | 20 | 10% sucrose, 2% raffinose | 1% Gelatin | 0.2% Pluronic F68 | 10 mM methionine, 100 mM 7.0 citrate buffer |
| AVS22 | 20 | 2% raffinose | 1% Gelatin | 0.2% Pluronic F68 | 10 mM methionine, 100 mM 7.0 citrate buffer |
| AVS23 | 20 | 10% raffinose | | 0.2% Pluronic F68 | 10 mM methionine, 100 mM 7.0 citrate buffer |
| AVS24 | 20 | 10% sucrose, 5% raffinose | 5% Gelatin | 0.1% Pluronic F68 | 10 mM methionine, 25 mM 7.2 KPO4 buffer |
| AVS25 | 20 | 15% sucrose | 5% Gelatin | 0.1% Pluronic F68 | 10 mM methionine, 25 mM 7.2 KPO4 buffer |
| AVS26 | 20 | 15% raffinose | 5% Gelatin | 0.1% Pluronic F68 | 10 mM methionine, 25 mM 7.2 KPO4 buffer |
| AVS27 | 20 | 10% sucrose, 5% raffinose | | 0.1% Pluronic F68 | 10 mM methionine, 25 mM 7.2 KPO4 buffer |
| AVS28 | 20 | 10% sucrose, 5% raffinose | 5% Gelatin | 0.1% Pluronic F68 | 2% ovalbumin, 10 mM methionine, 25 mM 7.2 KPO4 buffer |
| AVS29 | | 40% raffinose | 5% Gelatin | 0.1% Pluronic F68 | 10 mM methionine, 25 mM 7.2 KPO4 buffer |
| AVS30 | 10 | 40% sucrose | 5% Gelatin | 0.1% Pluronic F68 | 10 mM methionine, 25 mM 7.2 KPO4 buffer |
| AVS31 | 10 | 40% sucrose | 5% Gelatin | 0.1% Pluronic F68 | 10 mM methionine, 25 mM 7.2 KPO4 buffer, 1% glycerol |

-continued

| ID | Glutamate | Polyol | Polymer Additive | Surfactant | Other |
|---|---|---|---|---|---|
| AVS32 | 20 | 15% sucrose | 5% Gelatin | 0.1% Pluronic F68 | 10 mM methionine, 25 mM 7.2 KPO4 buffer |
| AVS33 | 20 | 15% sucrose | 1% Gelatin | 0.1% Pluronic F68 | 10 mM methionine, 25 mM 7.2 KPO4 buffer |
| AVS34 | 20 | 15% sucrose | | 0.1% Pluronic F68 | 10 mM methionine, 25 mM 7.2 KPO4 buffer |
| AVS35 | 20 | 20% sucrose | 5% Gelatin | 0.1% Pluronic F68 | 10 mM methionine, 25 mM 7.2 KPO4 buffer |
| AVS36 | 20 | 20% sucrose | | 0.1% Pluronic F68 | 2% ovalbumin, 10 mM methionine, 25 mM 7.2 KPO4 buffer |
| AVS37 | 10 | 20% sucrose, 10% raffinose | | 0.1% Pluronic F68 | 1% arginine, 10 mM methionine, 25 mM 7.2 KPO4 buffer |
| AVS38 | 20 | 20% sucrose | 1% Gelatin | 0.2% Pluronic F68 | 10 mM methionine, 25 mM 7.2 KPO4 buffer |
| AVS39 | 20 | 20% sucrose | 5% Gelatin | 0.005% Tween 20 | 10 mM methionine, 25 mM 7.2 KPO4 buffer |
| AVS40 | 20 | 20% sucrose | | 0.005% Tween 20 | 2% ovalbumin, 10 mM methionine, 25 mM 7.2 KPO4 buffer |
| AVS41 | 10 | 40% sucrose | 5% Gelatin | 0.02% Pluronic F68 | 10 mM methionine, 25 mM 7.2 KPO4 buffer |
| AVS42 | 10 | 40% sucrose | 5% Gelatin | 0.02% Pluronic F68 | 10 mM methionine, 25 mM 7.2 KPO4 buffer, 1% glycerol |
| AVS43 | | 40% sucrose | 5% Gelatin | 0.02% Pluronic F68 | 10 mM methionine, 25 mM 7.2 KPO4 buffer |
| AVS44 | | 40% sucrose | 5% Gelatin | 0.02% Pluronic F68 | 10 mM methionine, 25 mM 7.2 KPO4 buffer, 1% glycerol |
| AVS45 | 10 | 40% sucrose | 5% Gelatin | | 10 mM methionine,, 1% glycerol |
| AVS46 | | 50% sucrose | 1% Gelatin | | 10 mM methionine, 25 mM 7.2 KPO4 buffer, 1% glycerol |
| AVS47 | 10 | 40% sucrose | 5% Gelatin | 0.02% Pluronic F68 | 10 mM methionine, 25 mM 7.2 KPO4 buffer, 1% glycerol |
| AVS48 | | 40% sucrose, 5% trehalose | 5% Gelatin | 0.02% Pluronic F68 | 10 mM methionine, 25 mM 7.2 KPO4 buffer, 1% glycerol |
| AVS49 | | 40% sucrose | 3% Gelatin | 0.02% Pluronic F68 | 10 mM methionine, 25 mM 7.2 KPO4 buffer |
| AVS50 | | 40% sucrose | 1% Gelatin | 0.02% Pluronic F68 | 10 mM methionine, 25 mM 7.2 KPO4 buffer |
| AVS51 | | 40% sucrose | | 0.02% Pluronic F68 | 10 mM methionine, 25 mM 7.2 KPO4 buffer |
| AVS52 | | 40% sucrose | 5% Gelatin | | 10 mM methionine, 25 mM 7.2 KPO4 buffer |
| AVS53 | | 40% sucrose | | 0.02% Pluronic F68 | 25 mM 7.2 KPO4 buffer |
| AVS54 | | 40% sucrose | 5% Gelatin | | 25 mM 7.2 KPO4 buffer |
| AVS55 | | 20% sucrose | 5% Gelatin | 0.02% Pluronic F68 | 10 mM methionine, 25 mM 7.2 KPO4 buffer |
| AVS56 | | 10% sucrose | 5% Gelatin | 0.02% Pluronic F68 | 10 mM methionine, 25 mM 7.2 KPO4 buffer |
| AVS57 | | 40% sucrose | | 0.02% Pluronic F68 | 5% ovalbumin, 25 mM 7.2 KPO4 buffer |

-continued

| ID | Glutamate | Polyol | Polymer Additive | Surfactant | Other |
|---|---|---|---|---|---|
| AVS58A | | 40% sucrose | 5% Gelatin (Sigma AD) | 0.02% Pluronic F68 | 25 mM 7.2 KPO4 buffer |
| AVS58B | | 40% sucrose | 5% Gelatin Sigma (R) | 0.02% Pluronic F68 | 25 mM 7.2 KPO4 buffer |
| AVS59 | | 40% sucrose | 5% Gelatin | 0.02% Pluronic F68 | 10 mM methionine, 25 mM 7.2 KPO4 buffer |
| AVS60 | | 40% sucrose | 5% Gelatin | 0.02% Pluronic F68 | 10 mM methionine, 25 mM 7.2 KPO4 buffer |
| AVS61 | | 20% sucrose | 2.5% Gelatin | 0.01% Pluronic F68 | 5 mM methionine, 12.5 mM 7.2 KPO4 buffer |
| AVS62 | | 40% sucrose | | 0.02% Pluronic F68 | 5% arginine, 10 mM methionine, 25 mM 7.2 KPO4 buffer |
| AVS63 | | 40% sucrose | | 2.5% PEG 1000, 0.02% Pluronic F68 | 10 mM methionine, 25 mM 7.2 KPO4 buffer |
| AVS64 | | 40% sucrose | | 2.5% PVP 10,000, 0.02% Pluronic F68 | 10 mM methionine, 25 mM 7.2 KPO4 buffer |
| AVS65 | | 40% sucrose | | 2.5% Ficoll 400K, 0.02% Pluronic F68 | 10 mM methionine, 25 mM 7.2 KPO4 buffer |
| AVS66 | | 20% sucrose | 2% Gelatin | 0.02% Pluronic F68 | 10 mM methionine, 25 mM 7.2 KPO4 buffer |
| AVS67 | | 40% sucrose | 5% Gelatin | 0.02% Pluronic F68 | 1% methionine, 25 mM 7.2 KPO4 buffer |
| AVS68 | | 20% sucrose | 2% Gelatin | 0.02% Pluronic F68 | 1% methionine, 25 mM 7.2 KPO4 buffer |
| AVS69 | | 40% sucrose | | 0.02% Pluronic F68 | 5% arginine, 1% methionine, 25 mM 7.2 KPO4 buffer |
| AVS70 | | 20% sucrose | | 0.02% Pluronic F68 | 5% arginine, 1% methionine, 25 mM 7.2 KPO4 buffer |

The thermostability of the above formulations after post-lyophilization storage at 37° C. or 50° C. were measured. Increased thermostability can be observed as shown as a decrease in the rate of potency loss, measured as the log FFU/ml or TCID$_{50}$/ml. The time required for a one log order loss in FFU/ml are provided below for various formulations of the invention:

| Formulation | Stability at 37° C. |
|---|---|
| AVS43 | 125 days |
| AVS41 | 97 days |
| AVS44 | 142 days |
| AVS30 | 93 days |
| AVS31 | 48 days |
| AVS42 | 146 days |

Example 3

Foam Drying Conditions

Formulations were prepared using the following lyophilization/drying chamber conditions:

Cycle 1:

1) Pre-cool shelves to 25° C.;
2) Load vials and allow to equilibrate;
3) Set vacuum to 50 mTorr;
4) Hold for 30 minutes;
5) Ramp to 45° C.;
6) Hold for 1 hour;
7) Adjust the temperature to 37° C. and hold for 1 hour; and
8) Stopper vials.

Cycle 2:

1) Pre-cool shelves to 30° C.;
2) Load vials and allow to equilibrate;
3) Set vacuum to 50 mTorr;
4) Hold for 2 hours;
5) Ramp to 37° C.;
6) Hold for 16 hours; and
7) Stopper vials.

Cycle 3:

1) Pre-cool shelves to 15° C.;
2) Load vials and allow to equilibrate;
3) Set vacuum to 50 mTorr;
4) Hold for 60 minutes;
5) Ramp to 37° C.;
6) Hold for 20 hours; and
7) Stopper vials.

Cycle 4:

1) Pre-cool shelves to 12° C.;
2) Load vials and allow to equilibrate;
3) Set vacuum to 50 mTorr;
4) Hold for 25 minutes;
5) Ramp to 33° C.;
6) Hold for 24 hours; and
7) Stopper vials.

-continued

Cycle 5:

1) Pre-cool shelves to 17° C.;
2) Load vials and allow to equilibrate for 10 minutes;
3) Set vacuum to 50 mTorr;
4) Hold for 60 minutes;
5) Ramp to 37° C.;
6) Hold for 48 hours;
7) Ramp to 40° C.;
8) Hold for 48 hours; and
9) Stopper vials.

Cycle 6:

1) Pre-cool shelves to 20° C.;
2) Load vials and allow to equilibrate;
3) Set vacuum to 50 mTorr;
4) Hold for 60 minutes;
5) Ramp to 33° C.;
6) Hold for 72 hours; and
7) Stopper vials.

Example 4

Formulations

The drying cycle shown in Example 1 was employed to stabilize live B/Harbin influenza virus. The following table summarizes the observed stability profiles of these formulations after storage for ten months at 25° C.:

| Formulation | KPO4 buff. pH 7.2 (mM) | Sucrose (%) | Gelatin (%) | Methionine (mM) | Pluronic F68 (%) | Slope at 25° C. | Months to 1 log FFU/ml loss | Process Loss (Log FFU/ml) |
|---|---|---|---|---|---|---|---|---|
| AVS068 | 25 | 10 | 0 | 0 | 0.02 | −0.167 | 6 | 0.20 |
| AVS071 | 25 | 10 | 0 | 10 | 0 | −0.245 | 4.1 | 0.13 |
| AVS072 | 25 | 10 | 0 | 66.7 | 0.2 | −0.047 | 21.4 | 0.37 |
| AVS073 | 25 | 10 | 2 | 0 | 0.2 | −0.089 | 11.2 | 0.63 |
| AVS074 | 25 | 10 | 2 | 10 | 0.02 | −0.056 | 17.8 | 1.13 |
| AVS075 | 25 | 10 | 2 | 66.7 | 0 | −0.154 | 6.5 | 0.43 |
| AVS076 | 25 | 10 | 5 | 0 | 0 | −0.145 | 6.9 | 0.67 |
| AVS077 | 25 | 10 | 5 | 10 | 0.2 | −0.008 | 121.2 | 0.47 |
| AVS078 | 25 | 10 | 5 | 66.7 | 0.02 | −0.050 | 20.0 | 0.27 |
| AVS079 | 25 | 10 | 5 | 66.7 | 0.2 | −0.043 | 23.1 | 0.83 |
| AVS080 | 25 | 20 | 0 | 0 | 0 | −0.132 | 7.6 | 0.50 |
| AVS081 | 25 | 20 | 0 | 10 | 0.02 | −0.060 | 16.8 | 0.53 |
| AVS082 | 25 | 20 | 0 | 66.7 | 0.2 | −0.045 | 22.4 | 0.07 |
| AVS083 | 25 | 20 | 2 | 0 | 0.02 | −0.040 | 24.9 | 2.27 |
| AVS084 | 25 | 20 | 2 | 10 | 0 | −0.096 | 10.4 | 0.33 |
| AVS085 | 25 | 20 | 2 | 66.7 | 0.2 | −0.040 | 25.0 | 0.43 |
| AVS086 | 25 | 20 | 5 | 0 | 0.2 | −0.022 | 44.6 | 0.30 |
| AVS087 | 25 | 20 | 5 | 10 | 0.2 | −0.005 | 200.4 | 0.40 |
| AVS088 | 25 | 20 | 5 | 66.7 | 0 | −0.060 | 16.7 | −0.07 |
| AVS089 | 25 | 20 | 5 | 66.7 | 0.02 | −0.022 | 44.5 | 0.67 |
| AVS090 | 25 | 40 | 0 | 0 | 0.2 | −1.283 | 0.8 | 0.63 |
| AVS091 | 25 | 40 | 0 | 10 | 0.2 | −1.117 | 0.9 | 0.77 |
| AVS092 | 25 | 40 | 0 | 66.7 | 0 | −0.120 | 8.3 | 0.50 |
| AVS093 | 25 | 40 | 0 | 66.7 | 0.02 | −0.033 | 30.2 | 0.73 |
| AVS094 | 25 | 40 | 2 | 0 | 0 | −0.116 | 8.6 | 0.83 |
| AVS095 | 25 | 40 | 2 | 10 | 0.2 | −0.016 | 63.8 | 0.47 |
| AVS096 | 25 | 40 | 2 | 66.7 | 0.02 | −0.030 | 33.2 | 0.80 |
| AVS097 | 25 | 40 | 2 | 66.7 | 0.2 | −0.017 | 58.1 | 0.27 |
| AVS053s | 25 | 40 | 5 | 0 | 0.02 | −0.022 | 44.6 | 0.47 |
| AVS098 | 25 | 40 | 5 | 0 | 0.2 | −0.023 | 43.4 | 0.37 |
| AVS052b | 25 | 40 | 5 | 10 | 0 | −0.087 | 11.6 | 0.67 |
| AVS043c | 25 | 40 | 5 | 10 | 0.02 | −0.037 | 27.2 | 0.77 |
| AVS099 | 25 | 40 | 5 | 66.7 | 0 | −0.067 | 15.0 | 0.40 |

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, the formulations, techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

What is claimed is:

1. A method for preparing a dry foam composition comprising a bioactive material, which method comprises:
preparing a formulation comprising in a solvent: the bioactive material, a foaming agent, and a polyol or polymer;
expanding the formulation into a foam; and,
stabilizing or drying the foam by evaporating or sublimating the solvent from the foam;
thereby preparing a dry foam composition.

2. The method of claim 1, wherein the bioactive material is selected from the group consisting of peptides, proteins, nucleic acids, antibodies, vaccines, bacteria, viruses, liposomes, platelets, and cell suspensions.

3. The method of claim 2, wherein the viruses are live viruses selected from the group consisting of influenza virus, parainfluenza virus, AAV, adenovirus, respiratory syncytial virus, herpes simplex virus, cytomegalovirus, SARS virus, corona virus family members, human metapneumovirus, and Epstein-Barr virus.

4. The method of claim 1, wherein the foaming agent comprises a gas in solution in the formulation, a high vapor pressure solvent, a carbonate, an active metal, or a suspension of gas bubbles.

5. The method of claim 1, wherein the polyol is present in an amount ranging from about 20 weight percent to about 45 weight percent.

6. The method of claim 1, wherein the polyol comprises sucrose, trehalose, sorbose, melezitose, sorbitol, stachyose, raffinose, fructose, mannose, maltose, lactose, arabinose, xylose, ribose, rhamnose, galactose, glucose, mannitol, xylitol, erythritol, threitol, sorbitol, glycerol, or L-gluconate.

7. The method of claim 1, wherein the polymer is present in an amount ranging from about 1 weight percent to about 10 weight percent.

8. The method of claim 1, wherein the polymer comprises hydrolyzed gelatin, unhydrolyzed gelatin, collagen, chondroitin sulfate, water soluble polymers, polyvinyl pyrrolidone, a sialated polysaccharide, actin, myosin, microtubules, dynein, kinetin, or human serum albumin.

9. The method of claim 1, wherein expanding into a foam comprises, degassing the formulation, boiling the formulation, forming a gas by chemical reaction, forming bubbles by electrolysis, expanding bubbles suspended in the formulation, or injection of bubbles into the formulation.

10. The method of claim 1, wherein the formulation further comprises a surfactant or a buffer.

11. The method of claim 1, wherein the bioactive material comprises a lipid membrane, and wherein the method further comprises cooling the formulation to a phase transition temperature of the lipid membrane.

12. The method of claim 11, further comprising holding the formulation at the phase transition temperature for from about 10 minutes to about 60 minutes.

13. The method of claim 1, further comprising increasing the temperature of the formulation to a drying temperature that is less than or about the glass transition temperature of the dry foam.

14. The method of claim 1, further comprising grinding the dry foam to a powder comprising an average particle size from about 0.1 um to about 100 um.

15. The method of claim 14, wherein the a powder comprises an average particle size from about 50 um to about 100 um.

16. The method of claim 1, further comprising administering the dry foam composition to a mammal as a reconstituted liquid or as a ground powder.

17. The method of claim 16, wherein administering comprises delivering the composition to the mammal by intravenous, intramuscular, intraperitoneal, intracerebrospinal, subcutaneous, intra-articular, intrasynovial, intrathecal, oral, topical, intranasal, or pulmonary routes.

18. The method of claim 1, further comprising secondary drying the foam at a temperature from about 10° C. to about 70° C.

19. The method of claim 1, wherein said preparing the formulation comprises providing sufficient polyol so that a glass is formed upon said drying step.

20. The method of claim 1, wherein the expanding is other than by boiling.

21. The method of claim 1, wherein the foaming agent is other than the solvent.

22. The method of claim 1, wherein said expansion is by action of the foaming agent.

* * * * *